United States Patent [19]

Giordano

[11] 4,135,096
[45] Jan. 16, 1979

[54] ELECTRONIC-OPTICAL SYSTEM FOR X-RAY OBJECT CROSS SECTION IMAGE RECONSTRUCTION

[76] Inventor: Ames F. Giordano, 8 Crest View, West Orange, N.J. 07052

[21] Appl. No.: 854,265

[22] Filed: Nov. 23, 1977

[51] Int. Cl.² .............................................. G03B 41/16
[52] U.S. Cl. .................................. 250/445 T; 250/360
[58] Field of Search ............... 250/445 T, 358 R, 359, 250/360

[56] References Cited

U.S. PATENT DOCUMENTS 4,021,673  5/1977  Bossaert ........................... 250/445 T Primary Examiner—Craig E. Church

[57] ABSTRACT

An X-ray object cross section image reconstruction system wherein X-ray fan beam path attenuation signals, detected through a cross section layer of an object at a multiplicity of scan angles, modulate a laser scan light beam analog of the X-ray fan beam scan geometry. The laser light beam signals are optically rotated and directed according to the fan angle, forming spatial correlation centers in an image plane for each object cross section elemental volume. The light signal intensity at elemental points in the image plane is sensed and electrically integrated thereby detecting and exalting the elemental object attenuation correlated signals. Interfering object shadow superfluous spread distributions are corrected by an anticipatory correcting input signal dispersion forming opposing and normalizing spread distributions. The corrected cross section image is formed during X-ray scan for immediate display on a television monitor screen, and may be permanently recorded on a video tape recorder.

36 Claims, 47 Drawing Figures

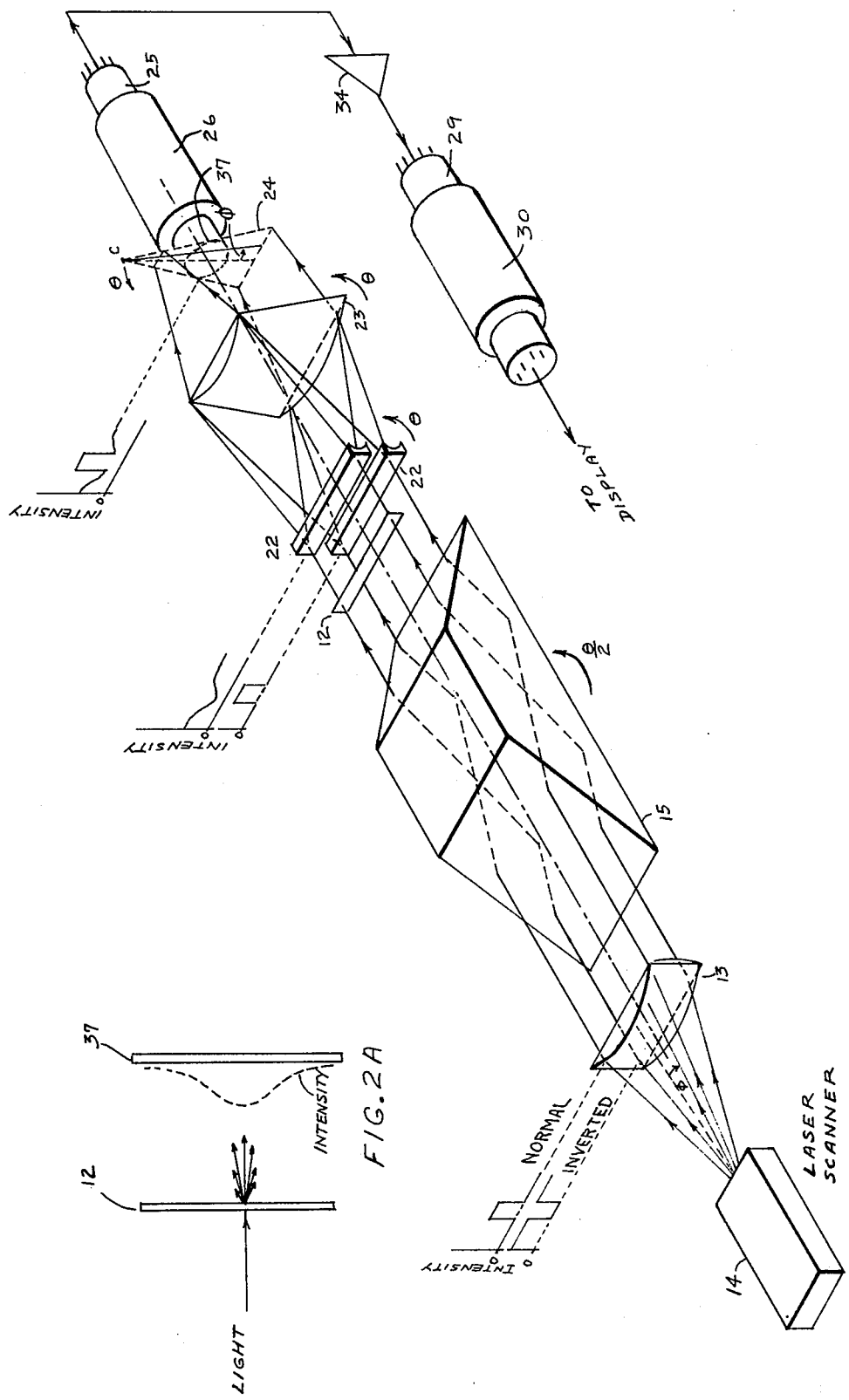

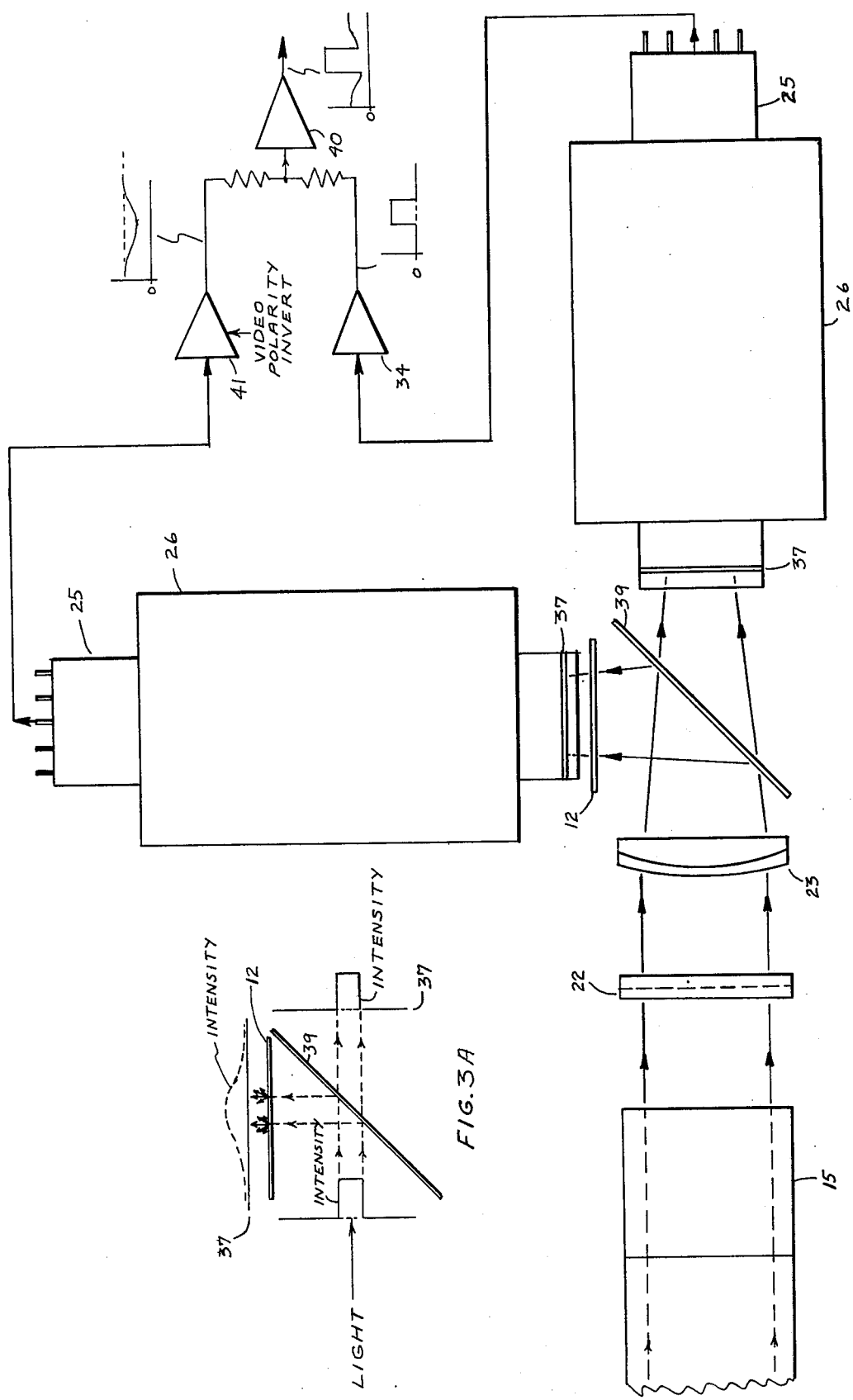

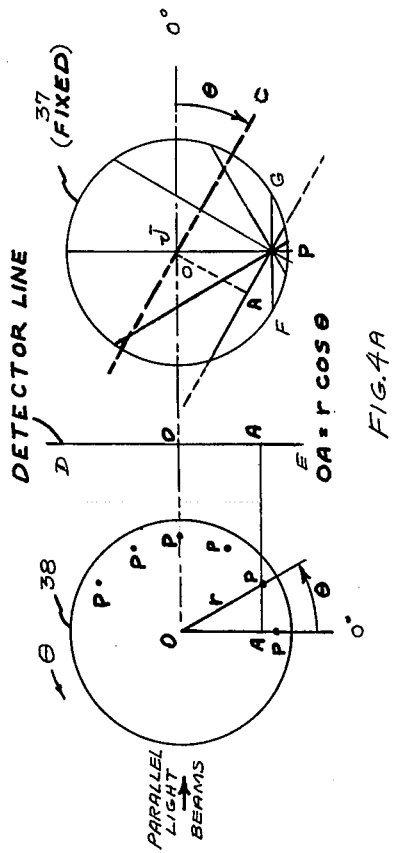
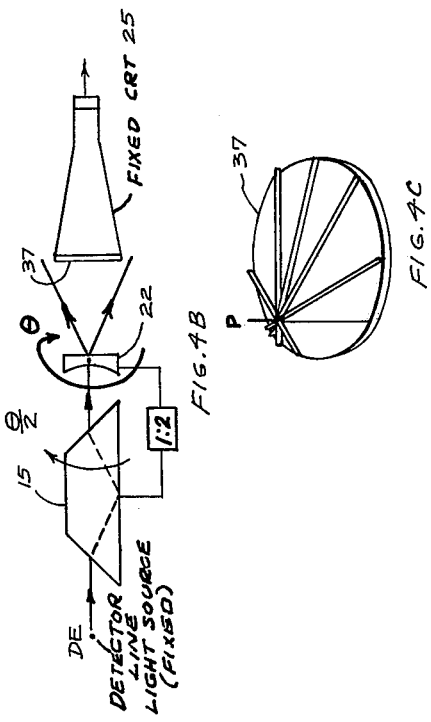
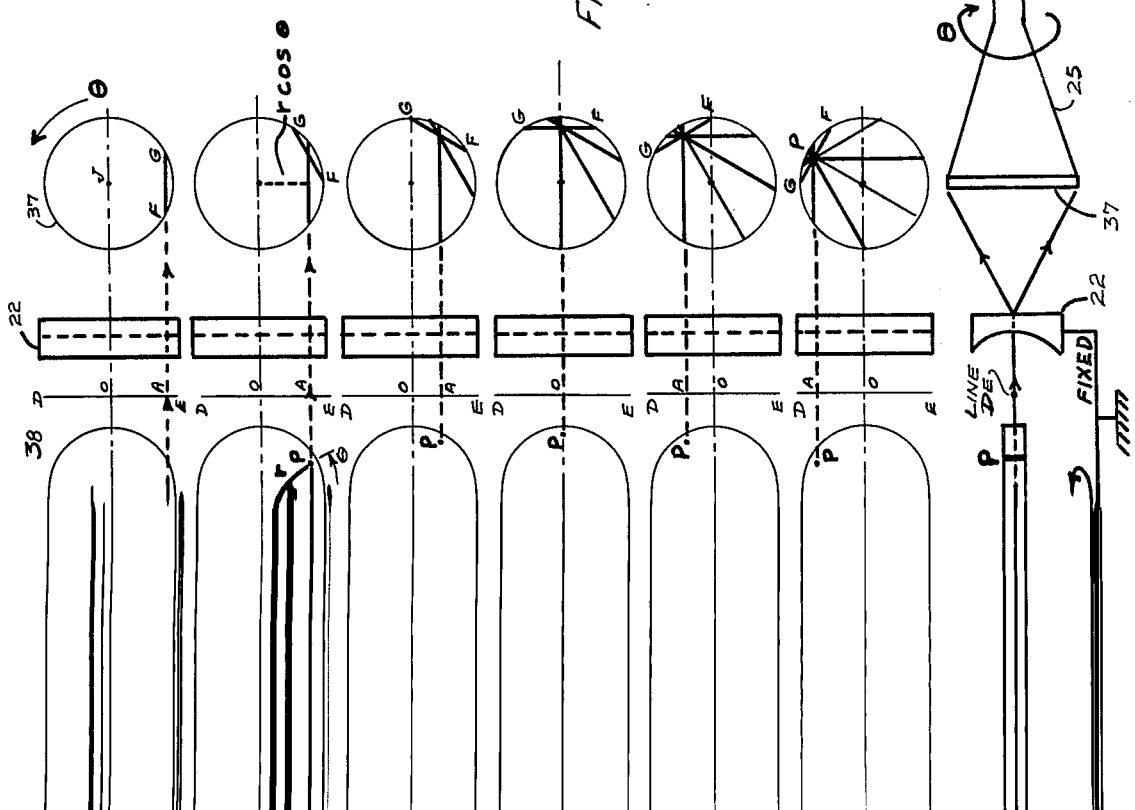

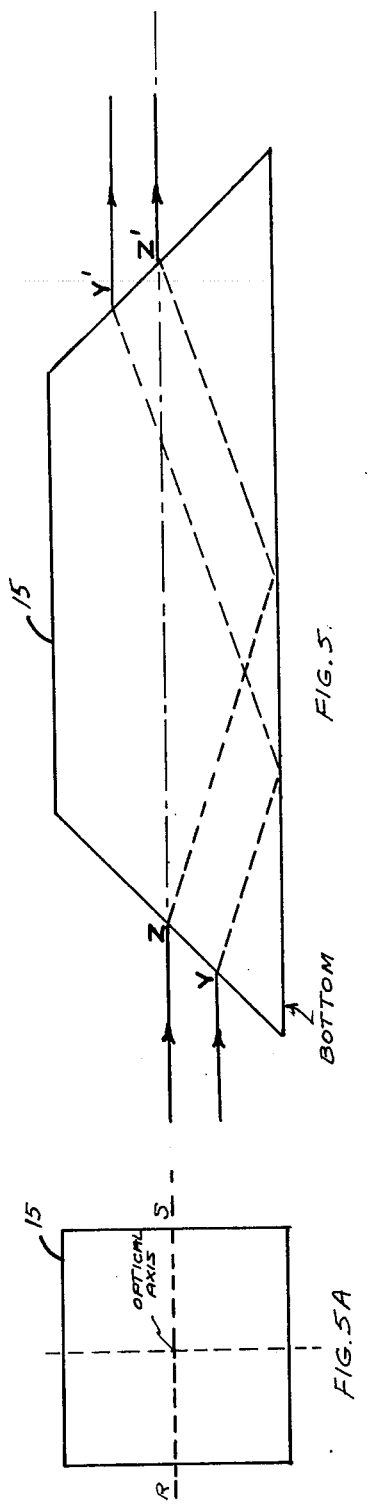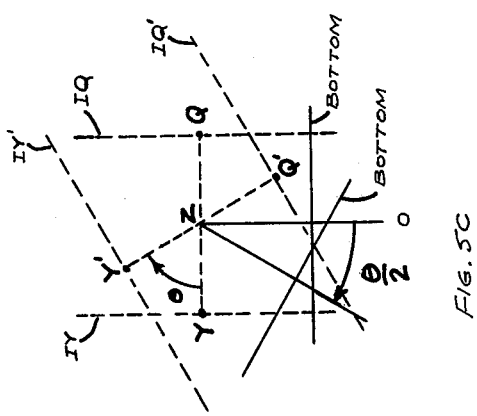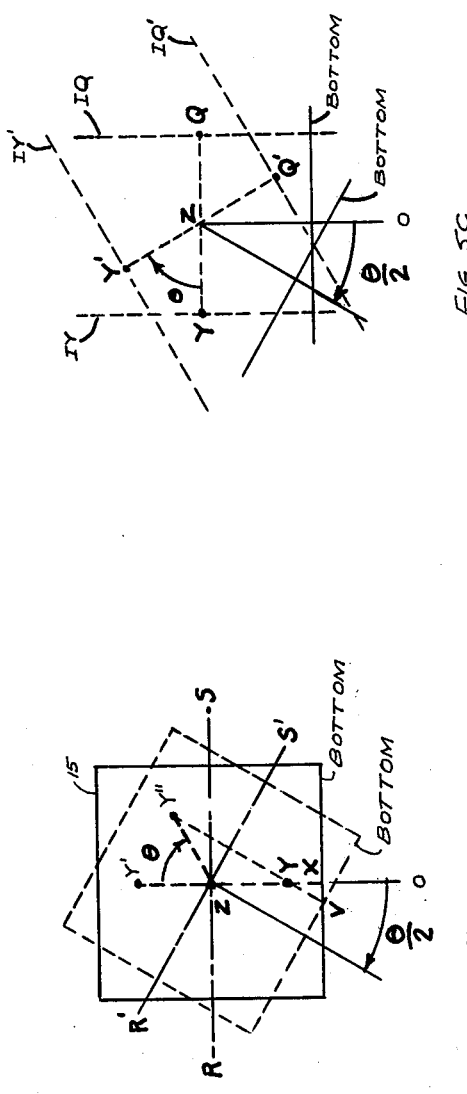

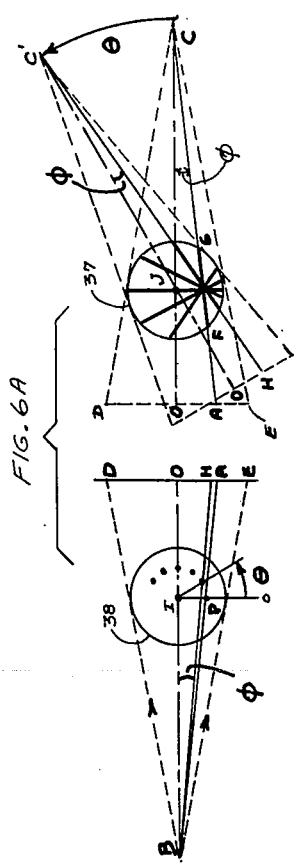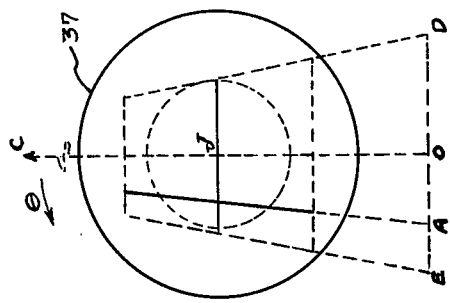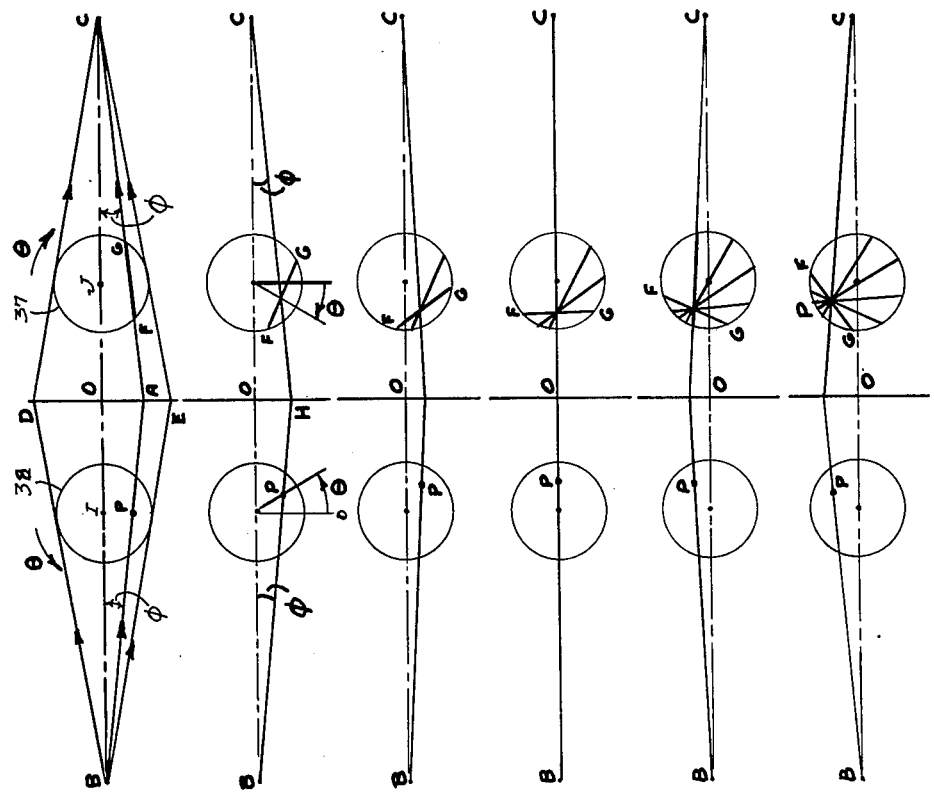
FIG. 6A
FIG. 6B
FIG. 6

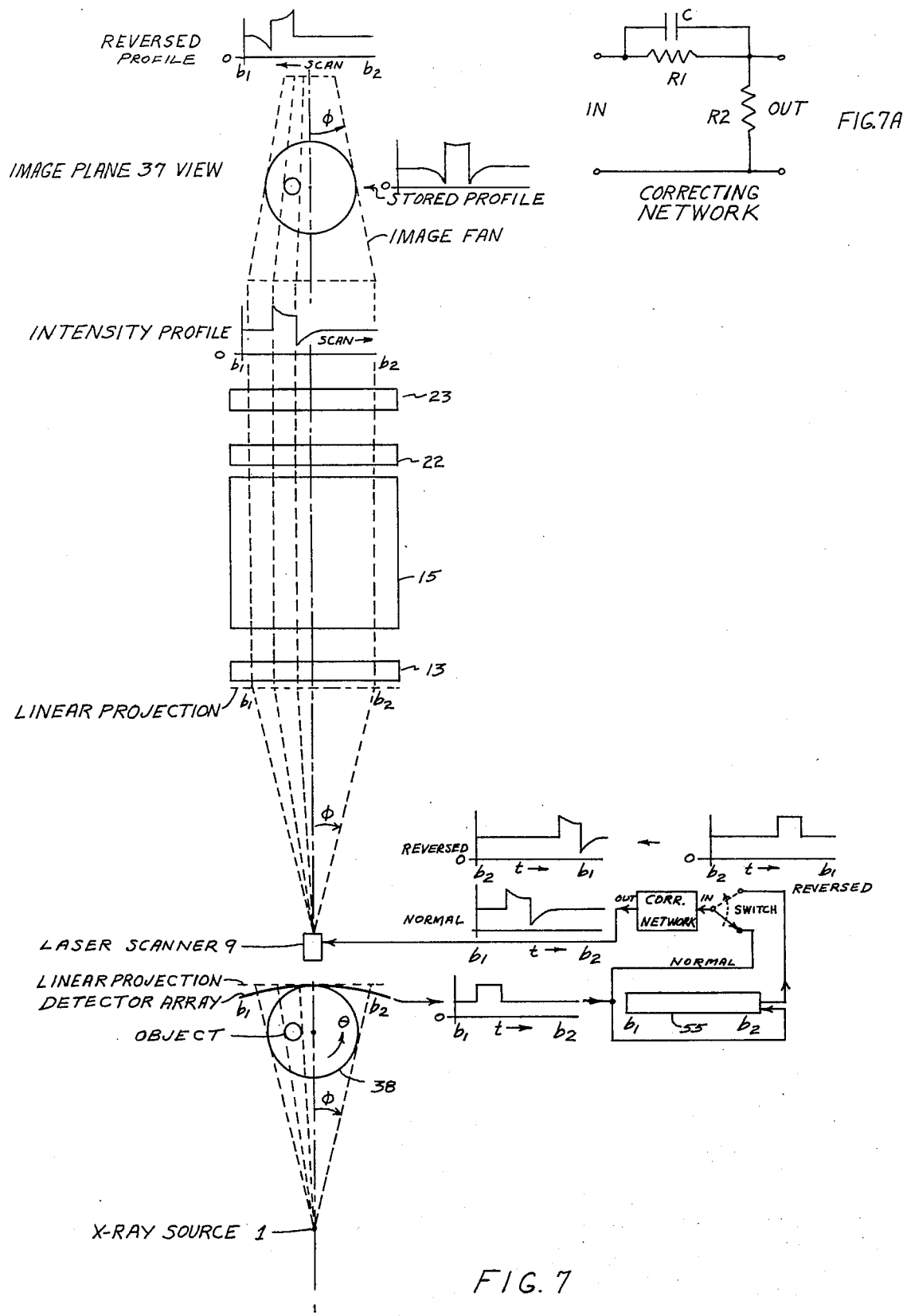

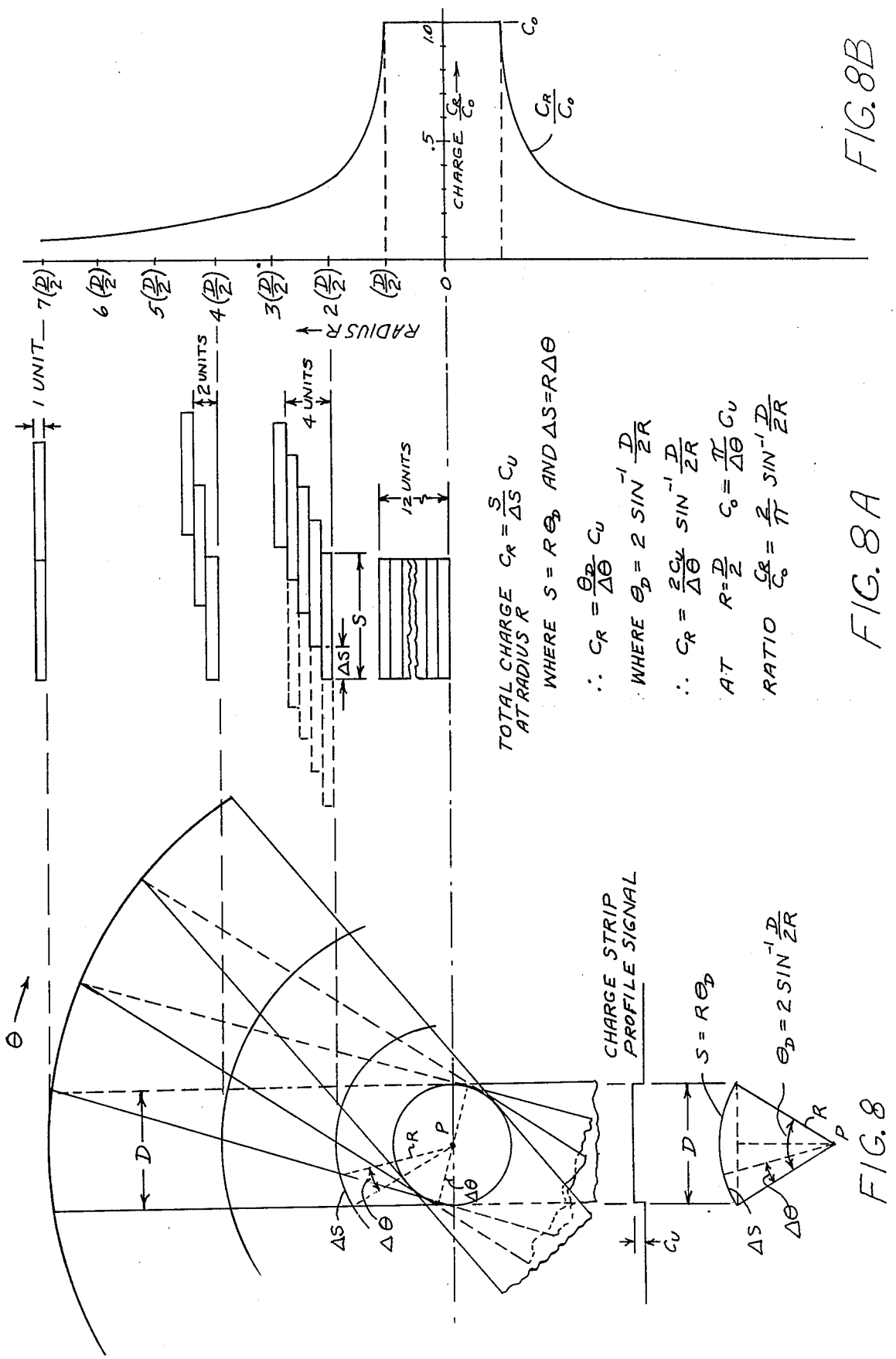

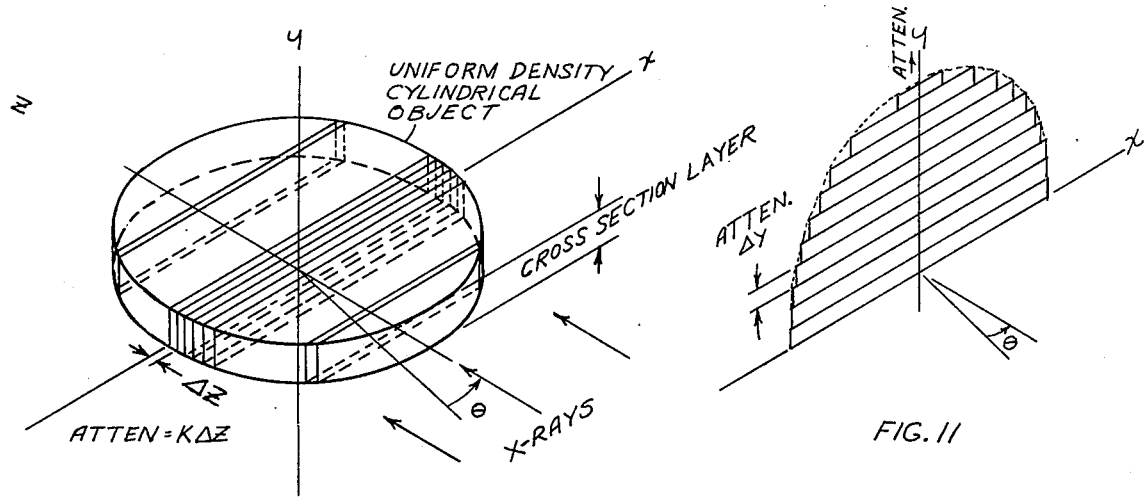
FIG.10
FIG.11
UNIFORM DENSITY OBJECTS
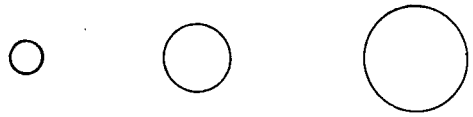
FIG. 12
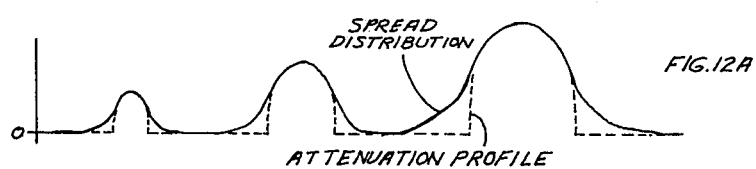
FIG.12A
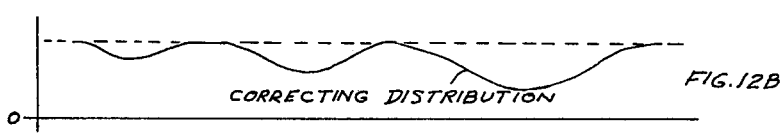
FIG.12B
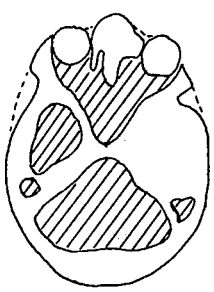
FIG.13
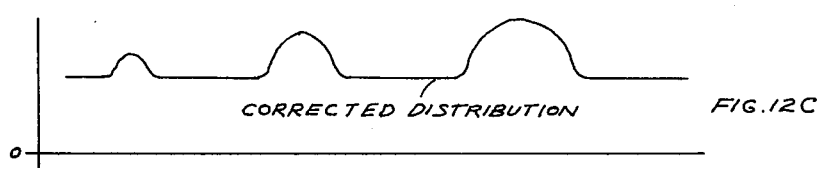
FIG.12C

ELECTRONIC-OPTICAL SYSTEM FOR X-RAY OBJECT CROSS SECTION IMAGE RECONSTRUCTION

This invention relates to x-ray imaging systems and more particularly to an electronic-optical system for x-ray object cross-section image reconstruction.

X-ray images of cross-sectional layers through a human object portray the structure and organs and reveal abnormalities such as tumors and their location. Images of several adjacent cross-section layers serve to localize a tumor more exactly. Various x-ray cross-section image reconstruction systems are known, wherein the cross-section layer is analyzed with x-rays at many angles thereby obtaining x-ray shadows or projections of objects within the layer. Using sensitive x-ray detectors, detecting narrow beams of x-rays, x-ray beams path attenuations are measured through the cross-section at many angles of scan to effectively obtain many path measurements through each elemental object in the cross-section. In 1917, J. Radon, a mathematician, proved mathematically that a three-dimensional object could be reconstructed from an infinite set of the objects' projections from all viewpoints. Since x-rays travel in straight lines, the internal cross-sectional features are projected where there are differences in x-ray attenuation due to object cross-section variations in density. Known x-ray cross-section image reconstruction systems utilize these multiple view x-ray attenuation projection profile sets of data in various ways to reconstruct an x-ray density image of the cross-section and is referred to as axial tomagraphy, being performed about the longitudinal axis of the human object.

In typical known computerized axial tomagraphy systems, the x-ray detector signals are obtained for a 180° or 360° scan about the human cross-section, requiring from six to 20 seconds for fast systems. These signals are received by a special purpose digital computer which requires on the order of two minutes of computation time for image reconstruction. Typical known digital computer reconstruction systems must store on the order of one million bits of x-ray detector data received in a 20 second cross-section scan, before computer reconstruction can begin. Reconstruction requires millions of computer operations on the stored x-ray detector signals for coordinate transformation, correction from mutually interfering shadow spread by cross-section objects, and trial and error computations to obtain an image having attenuation projections of best match of the original object attenuation projection data. The reconstructed image is then read out and displayed on a television monitor screen as shades of grey according to x-ray density.

A typical known computerized system utilizes an x-ray tube and opposing detectors traversing laterally so as to obtain path attenuation signals of parallel x-ray beams through a cross-section layer. This is repeated at small incremental angles of rotation around the human object.

Another typical known system utilizes an x-ray tube and an opposing arc of x-ray detectors so as to obtain simultaneous path attenuation signals of a fan pattern of x-ray beams through a cross-section layer. This is repeated at small incremental angles of rotation around the human object, the advantage being continuous and fast rotation, less image error due to human object breathing and organ motion, and reduced x-ray dosage.

In known computerized x-ray cross-section image reconstruction systems, the human patient either must be kept on the x-ray table while waiting for the computer image reconstruction or a series of cross-sections are taken assuming that they will show the desired information. The extensive computations in the computer are essentially performed serially, each sequence using the results of the previous sequence in a trial and error procedure thus requiring extensive image reconstruction time. Such systems require extensive equipment, are very complex, are costly, and do not construct images in real time.

Typical known optical x-ray cross-section image reconstruction methods use photographic film to record the multiple views through the cross-sections, which, after film development processing, are manipulated optically in various ways essentially reprojecting the film views back to a cross-section viewing plane. This method involves high x-ray dosage for film exposure, the processing time of hundreds of film profiles, critical film characteristics, and time consuming and laborious image correction, if any.

Accordingly, it is an object of this invention to provide an x-ray object cross-section image output on a television monitor in a reconstruction system which utilizes less equipment, is less complex, and at lower cost than presently known systems.

Another object of this invention is to provide an x-ray object cross-section image reconstruction system, which provides image reconstruction correction for mutually interfering shadow spread caused by cross-section objects.

Another object of this invention is to provide an x-ray object cross-section image reconstruction system which operates in real time from x-ray detector signals forming a reconstruction and providing a completed reconstructed cross-section image display immediately upon completion of generation of the x-ray detector signals.

Another object of this invention is to provide an x-ray object cross-section image reconstruction system which generates object cross-section images faster than presently known systems.

Another object of this invention is to provide an x-ray object cross-section image reconstruction system which has means for recording the object's cross-section projection profiles, during the real time reconstruction, for later reference and playback reconstruction.

This invention provides a means of generating and utilizing the x-ray detector signals from a rotary pulsed x-ray fan beam scanning apparatus to reconstruct a corrected object cross-section x-ray image during a fast scan for immediate display. This is accomplished in this invention by a combination of a modulated scanning laser light beam signal analog of the object modulated x-ray beam signals, a synchronously rotating optical assembly which directs the light beam signals to an image plane to form stationary signal correlation points for each cross-section point, a means for directing light beam signals into neighboring image plane points forming anticipatory opposing spread to normalize and correct for cross-section object shadow image spread, a light sensitive electrical integrating storage surface in the image plane which integrates the spatially correlated light beam signals and the correcting light beam signals forming a reconstructed image as an electrical amplitude distribution, and means for scan read-out of the distribution to a television type display. The rotary optical assembly includes a conical type lens for a given x-ray fan beam angle and which refracts and images the light beam signals to form a fan pattern in the image plane analogous to the fan pattern of x-ray beams. Various x-ray fan included angles can be accommodated with a corresponding conical lens and laser beam scan angle.

A feature of the invention is the real time reconstruction of object cross-section images for immediate display to observe any abnormalities and determine the most useful cross-section images.

Another feature of the invention is the rapidity of cross-section image reconstruction which minimizes image distortion due to object motion.

Another feature of the invention is correction for object shadow spread where an object light beam signals are dispersed to generate gaussian-like distributions which closely match and oppose the cross-section object's shadow spread.

Another feature of the invention is the use of the x-ray beam detector object cross-section attenuation signals to generate intensely modulated light beams in a fan pattern as an analog of the fan of object attenuated x-ray beams. The light beam signals are generated at the known angle of spacing of the detected x-ray beams. The fan of light beam signals generates a linear projection objection attenuation beam intensity profile through a line perpendicular to the mid-line of the fan of the light beam signals.

Another feature of the invention is a positive cylindrical lens disposed at the aforementioned perpendicular line so as to collimate the fan of light beam signals and convey the object cross-section attenuation profile as parallel light beam signals in a plane towards an image plane perpendicularly disposed.

Another feature of the invention is a rotatable dove prism which is driven to rotate the plane of the light beam signals about the central light beam and to rotational angles equal to the ratational angle of the x-ray beam fan pattern about the object cross-section.

Another feature of the invention is a negative cylindrical lens which is rotated in synchronism with the x-ray fan pattern and which intercepts and uniformly diverges the light beam signals into parallel planes of diverging light ray signals.

Another feature of the invention is conical-type lens which is coupled with the negative cylindical lens and which intercepts the parallel planes of diverging light ray signals and which are refracted and imaged to form a rotating fan pattern of image line signals in the image plane, which is analogous to the rotating x-ray beam fan pattern through the object cross-section. Each light beam signal from the linear projection attenuation profile is imaged as a uniform intensity image line signal along a path analogous to the corresponding x-ray beam path. An elemental object volume in the object cross-section attenuating x-ray beams generates corresponding light beam signals which form corresponding image line signals which intercept and define the elemental object location in the image plane. All cross-section points are thus correlated to corresponding stationary correlated points in the image plane.

Another feature of the invention is the disposition in the image plane of a light sensitive electrical integrating storage means such as a return beam vidicon cathode ray tube. The intensities of the image line signals are integrated at the correlation points thereby exalting the correlated signal level above the level of the non-correlated image line signals. For increasing size objects in the cross-section, image line signal strips formed are partially correlated radially around the desired correlated object image, causing superfluous shadow spread interference to other objects.

Another feature of the invention is the television type scan readout of the stored reconstructed image for display on a television type display monitor.

Another feature of the invention is the generation of a second set of light beam signals from inverted polarity x-ray detector signals thereby providing an inverted polarity linear projection attenuation beam intensity profile. The x-ray detector signals at each rotational angle are temporarily held for the second profile generation immediately following the normally generated profile. The second set of light beam signals are generated in a plane adjacent to the plane of the first set, and a second like negative cylindrical lens diverges the inverted polarity light beam signals to form inverted polarity image line signals in register with the normally generated image line signals. A light dispersing filter is disposed in front of the second negative cylindrical lens. The filter has a light dispersing characteristic which causes the inverted polarity image lines to have gaussian type shaped intensity profiles which increase in amplitude and width as an object size increases, to provide proportionate image corrections. The gaussian profiles correlate and integrate to like gaussian profiles of revolution providing predictable image correction.

Another feature of this invention provides an alternate method of generating the inverted gaussian image correction. Two television type vidicons which have temporary image storage characteristics are disposed in the image plane region wherein a 45 degree partial mirror provides the image plane image to both vidicons. The outputs of the vidicons are summed in a summing operational amplifier. One vidicon is operated with a light dispersing light filter disposed in front of it and the vidicon output is polarity inverted prior to the summing amplifier. The summing amplifier output during vidicon scan readout is stored and integrated point by point in a digital memory or in an electrical recording storage cathode ray tube.

Another feature of this invention is another method for generating the inverted gaussian image correction. The x-ray detector signals for each rotational angle are read out sequentially into a differentiating network. The resultant image signal lines are temporarily stored on a vidicon target. The x-ray detector signals are then read out in reverse sequence and like differentiated, generating light beam signals in a corresponding reverse direction scan. The differentiation network responds to the cross-section object size and density and forms light beam signal profiles which storage integrate as a profile one would obtain by adding an inverted gaussian profile to the object's profile. The correlation and integration of these profiles as transferred to long-term storage is equivalent to separately correlating and integrating an inverted Gaussian and normal object profiles for image correction.

Another feature of this invention is the use of a television type vidicon, which has temporary storage, instead of the return beam vidicon. The temporarily stored fan patterns for each x-ray fan beam rotational angle are read out to a long-term digital integrating storage memory or to an electrical recording integrating storage cathode ray tube.

The above-mentioned and other features and objects of this invention will become more apparent by reference to the following description taken in conjunction with the accompanying drawings, in which:

FIG. 2 illustrates another embodiment of the electro-optical signal correlator and integrator section of the embodiment of the invention shown in FIG. 1;

FIG. 3 illustrates another embodiment of the image plane sensing and integrating section of the embodiment of the invention shown in FIG. 1;

FIG. 4 is a sequence of diagrams which facilitate an explanation of the principles of the invention;

FIG. 4A illustrates signal correlation geometry on a fixed surface in accordance with principles of the invention;

FIG. 4B is a side view of the electro-optical elements which facilitates the description of the implementation of the geometrical construction of FIG. 4A;

FIG. 4C illustrates the spatial signal correlation and integration on an electrical storage target;

Figure 9A:
Figure 9B:
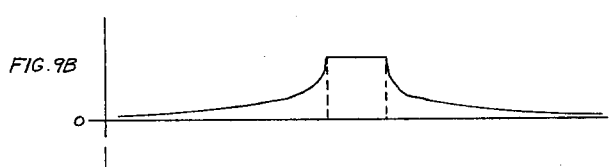
Figure 9C:
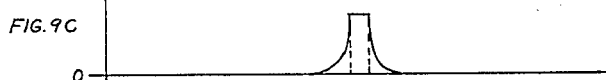
Figure 9D:
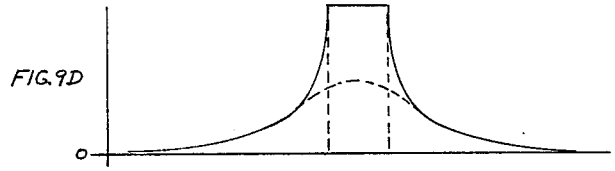
Figure 9E:
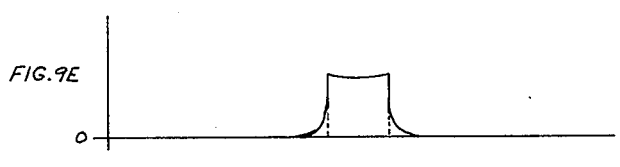
Figure 9F:
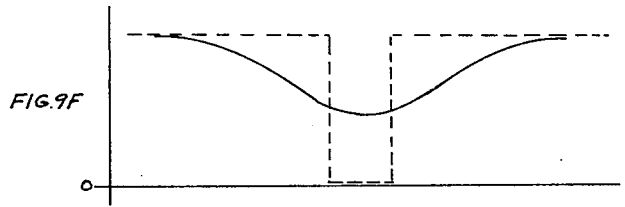
Figure 9G:
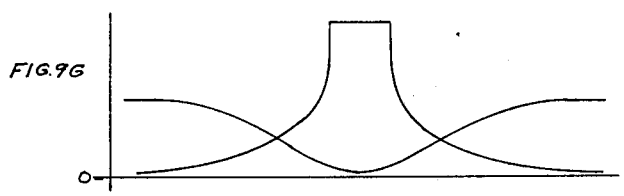
Figure 9H:
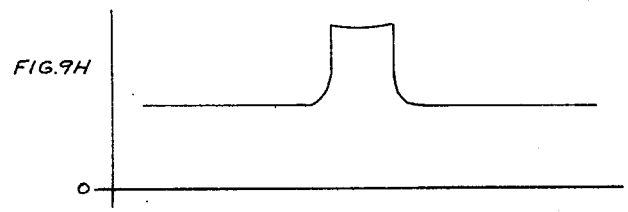
Figure 9I:
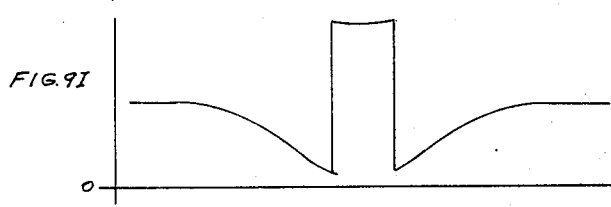
Figure 9J:
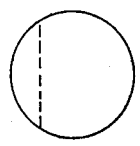
Figure 9K:
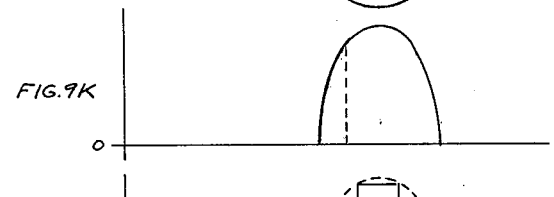
Figure 9L:
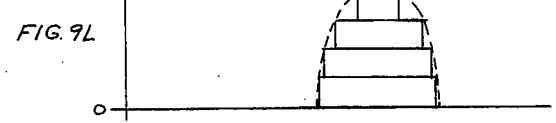
Figure 9M:
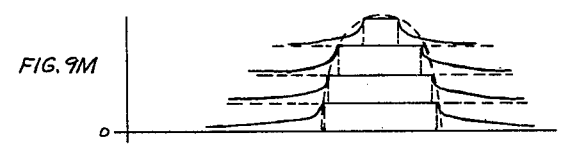
Figure 9N:
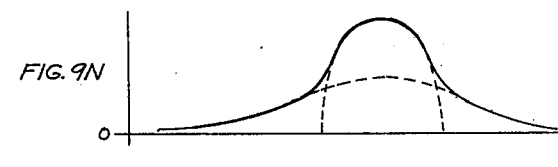
Figure 9O:
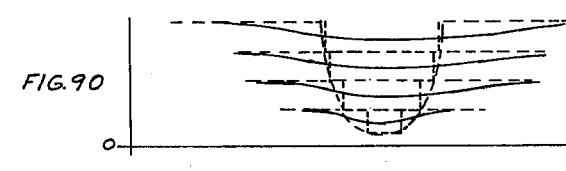
Figure 9P:
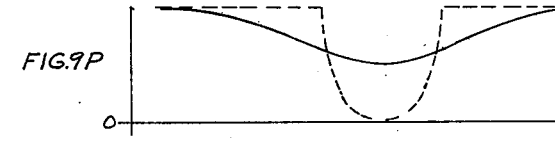
Figure 9Q:
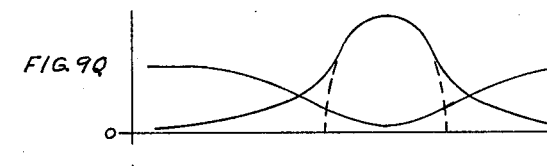
Figure 9R:
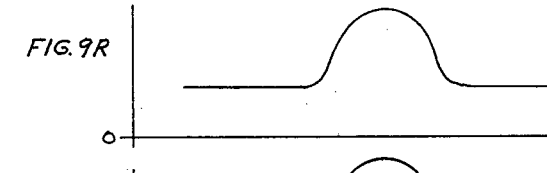
Figure 9S:
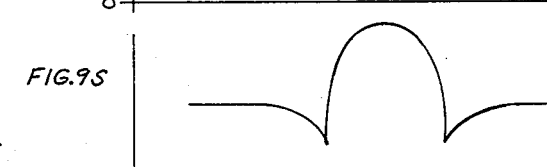

FIGS. 5, 5A, 5B, and 5C illustrate the light beam paths in a dove prism in accordance with the principles of the invention;

FIGS. 6, 6A and 6B are related diagrams which illustrate the principle of signal correlation of the invention for x-ray beams in a fan pattern;

FIGS. 7 and 7A illustrate a means of compensation for image reconstruction in accordance with the invention; FIGS. 8, 8A and 8B are diagrams which facilitate an explanation of the system response of correlation and integration in accordance with the invention;

FIGS. 9A through 9S are signal profiles which facilitate an explanation of the system responses and image correction in reconstruction in accordance with the invention;

FIGS. 10 and 11 are diagrams which facilitate an explanation of image correction in reconstruction, in accordance with the invention;

FIGS. 12 through 12C are a series of diagrams which illustrate the system responses for uniform density objects in accordance with the invention; and FIG. 13 is a simplified outline drawing of a typical human head cross-section image which could be reconstructed in accordance with the invention.

Figure 1:
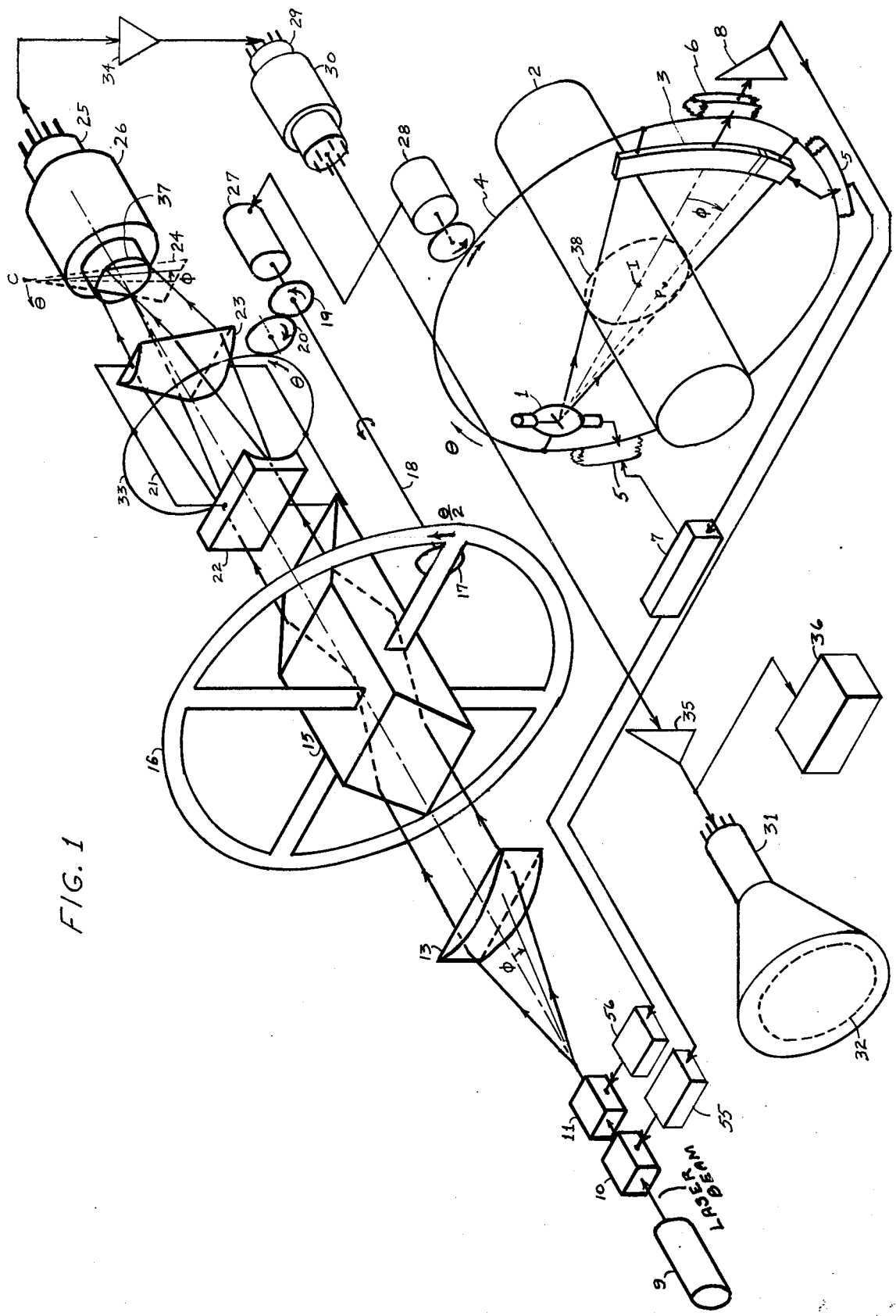
FIG. 1 is a perspective view and diagram of one embodiment of the x-ray object cross-section image reconstruction system in accordance with the invention.

Referring to FIG. 1, there is shown an x-ray tube point source 1 projecting a fan of x-rays through a cross-section 38 of a stationary object 2. X-ray detector array 3 consists of a multiplicity of x-ray detectors, each sensing the object path attenuation of a small diameter beam of x-rays at angles $\phi$ with respect to a line through the center of rotation I, forming a fan pattern of x-ray beams. The x-ray detector array utilizes high sensitivity crystal detectors or other suitable x-ray detectors. Each detector has a signal amplifier and a level hold circuit. The x-ray tube and detector array are attached to a suitable framework 4 which rotates by angle $\theta$ about the longitudinal axis of the object through point I in the cross-section 38. Electronic switches in the detector array sequentially connect the signal hold circuit outputs to a single line which feeds output amplifier 8 by means of a suitable slip-ring assembly 6. A detector selector 7 provides control signals through a slip-ring 5 which periodically pulse on the x-ray tube at small incremental angles of rotation and operate the electronic switches for sequential readout of the x-ray detector signals to shift register 55. Laser 9 emits a small diameter light beam through a beam intensity modulator 10 and beam deflector 11. Detector selector 7 provides control signals through deflection control unit 56 to control the laser beam deflector for sequential laser beam deflection in synchronism with the selected x-ray detectors and at angles $\phi$ corresponding to angles $\phi$ of the x-ray detectors. Shift register 55 is a signal recirculating register which is used in conjunction with image correction means and is described in later sections in connection with image correction embodiments of the invention whereby each x-ray detector signal sequence is recirculated for a second laser beam modulation sequence. In the embodiment of FIG. 1, the x-ray detector signal sequence from amplifier 8 is applied directly to the laser beam intensity modulator 10 via a bypass channel in shift register 55. The laser light beam signal intensity is proportionally modulated by the x-ray beam path attenuation detector signals. The laser light beam signal scan from the deflector 11 output describes a fan pattern which is a light beam analog of the detected fan pattern of object path attenuated x-ray beam. For example, if the x-ray detector array contains 500 detectors detecting a fan pattern of 500 x-ray beams, the laser light beam correspondingly and synchronously scans in a light beam fan pattern of 500 beam locations and with a beam width proportional to the x-ray beam widths. The main optical axis shown in FIG. 1 from the deflector 11 to cathode ray tube 25 corresponds to the line from x-ray point source 1 projected through the center of rotation I. Positive cylindrical lens 13 is disposed to intercept the fan of light beam signals along a line perpendicular to the main optical axis. The light beam signals through this line form a light beam signal intensity profile analog of the linear projection x-ray attenuation profile of the object cross-section for each x-ray beam fan pattern rotational angle $\theta$ of x-ray fan pulse-on. Lens 13 has a focal length such to refract the fan pattern of light beams projected from the point of deflection at deflector 11 to form collimated parallel light beam signals in a plane and towards image plane 24. Prism 15 is a dove prism which is disposed to intercept and rotate the plane of parallel light beam signals about the main optical axis to angles corresponding to and in synchronism with the x-ray beam fan pattern rotational angle $\theta$. A suitable framework 16, rotated within a suitable ring bearing, supports and rotates prism 15 about the prism's longitudinal axis of image rotation which is coincidental with the main optical axis. The parallel light beam signals intercepted by the dove prism are always refracted internally towards the bottom surface, reflected from the bottom, and refracted back to parallelism at the prism output surface, effectively displacing and rotating the plane of parallel light beams by an angle equal to twice the angle of prism rotation. Accordingly, prism 15 is driven to one-half the x-ray beam fan pattern angle $\theta$. Negative cylindrical lens 22 and positive conical lens 23 are rigidly coupled by framework 21 and rotated about the main optical axis by ring 33. Ring 33 rotates within a ring bearing and is one-half the diameter of framework 16. Drive wheels 17, 19, and 20, drive ring 33 to rotational angles $\theta$ equal to the x-ray beam fan pattern rotational angle $\theta$, and framework 16, in the same direction, to one-half angle $\theta$. Motor 27, is servo-controlled to follow motor 28 which drives x-ray apparatus framework 4. The cylindrical axis of lens 22 is kept in alignment with the rotated plane of parallel light beams at the output of dove prism 15. Lens 22 intercepts the parallel light beam signals and uniformly diverges each light beam signal into a diverged light ray signal plane perpendicularly to the plane of the input parallel light beam signals, forming parallel planes of diverged light ray signals. Positive conical lens 23 intercepts the parallel planes of diverged light ray signals, refracting and imaging the planes to form a fan pattern 24 of image line signals in image plane 37. Fan pattern 24 is produced at each rotational angle $\theta$ corresponding to the x-ray beam fan pattern rotational angle $\theta$. As the sequence of x-ray detector signals modulate the scanning laser beam, the image line signals are sequentially formed in the image plane fan pattern. The directions of laser beam scan and fan pattern image rotation are such that a point P in the object cross-section, intercepting an x-ray beam at angle $\phi$, generates a uniform intensity image line signal at angle $\phi$ which passes through a corresponding stationary point P in the image plane 37 for each successive fan pattern rotational angle $\theta$ thus forming image line signal correlation points which map the object cross-section in the image plane. In the embodiment of the invention of FIG. 1, cathode ray tube 25 is a television-type vidicon with deflection/focus coil assembly 26. The light sensitive vidicon target in image plane 37 integrates the sequence of image line signals intensity at all points to form a temporary stored charge amplitude fan pattern image during cathode ray beam blanking. The held x-ray detector signals are read out as a sequence to a fast laser beam scan forming a fan pattern of image line signals within a brief interval of time for target storage. During the time the x-ray apparatus is rotating to the next incremental angle of x-ray pulsing, the temporarily stored image line signal fan pattern on the vidicon 25 target is destructively read out with a television-type raster scan by the vidicon electron beam. The vidicon 25 video output is amplified by amplifier 34 and is used to modulate the electron beam of an electrical recording storage cathode ray tube 29, the target of which is like raster-scanned in synchronism with vidicon 25. Recording cathode ray tube 29 has a dielectric charge storage target which integrates the recorded charge amplitude at each target point for successive fan pattern images transferred from vidicon 25. In embodiment of the invention of FIG. 1, x-ray beam fan pattern pulsing at one degree increments over a total rotational angle of 179 degrees provides 179 path attenuation signals through each elemental volume in the object cross-section layer. The 180th path would be coincident with the first path but in the opposite direction. Rotational x-ray views beyond 179 degrees can also be generated to obtain additional symmetrical object element path data to compensate for x-ray scatter and fan beam tapering effects. An elemental object volume in the object cross-section intercepting and attenuating x-ray beams for the multiplicity of x-ray beam fan patterns, generates corresponding image line signals of intensity proportional to x-ray beam attenuation, intersecting and spatially correlating at corresponding image centers of correlation. The temporarily stored image line signal intensities are scan read out and transferred and integrated on the recording storage cathode ray tube target. At the signal correlation center the integrated charge is approximately the sum of 179 stored signal lines, or 179 times the elemental object volume x-ray beam attenuation. An elemental object volume is approximately the size of the x-ray beam width, a second elemental object volume at a distance from the first will occupy at least one x-ray beam path common to both causing one part in 179 mutual signal line interference, or spread, due to object shadowing. As an attenuating object volume increases in size more x-ray beams are intersecting and generate image signal strips intercepting at the object's correlation center. The intensity profile of the image signal strip is proportional to the length of the x-ray beam object attenuation path. If an x-ray opaque cylindrical volume is in the cross-section layer a rectangular image signal strip intensity profile is generated which is correlated and integrated having a charge distribution on the electrical storage surface shaped as a cylinder with decreasing superfluous charge spread amplitude in radial directions. I have calculated and experimentally verified that the spread amplitude is proportional to the arc sine of the ratio of the object cylinder radius to the radial distance to the center of correlation. This is the fully excited basic response of the system for the correlation and integration of a rectangular object attenuation profile. The larger the object volume diameter the greater the charge spread amplitude at given radial distances. I have observed that this charge amplitude distribution of the basic system response can be closely approximated by a gaussian-shaped amplitude distribution with a cylindrical amplitude distribution superposed. Furthermore, I have found that a gaussian-shaped intensity profile image signal strip correlates and integrates to a like gaussian-shaped charge amplitude distribution with no superfluous charge amplitude spread distribution. Thus, adding an inverted gaussian-shaped intensity profile to the normal intensity profile provides superfluous spread correction in the final correlated and integrated charge amplitude distribution. In other embodiments of the invention to be described, the correcting inverted gaussian is generated from the normal x-ray attenuation profile whereby the amplitude and width of the correcting gaussian profile increases with object diameter so as to closely follow the like increase in superfluous spread with object size. This will be described in later sections. In the embodiment of the invention of FIG. 1, the uncorrected correlated and integrated charge amplitude distribution on the electrical dielectric storage target of cathode ray tube 29 is read out by a television-type raster scan of the electron beam, amplified by video amplifier 35 and displayed as an uncorrected gray scale image of the reconstructed object cross-section on television monitor cathode ray tube 31. A hard copy recorder 36 provides a conventional means of recording the reconstructed image on a photosensitive medium for a permanent record. A conventional magnetic tape video recorder could also be utilized to permanently record the reconstructed cross-section images read out from the cathode ray tube 29.

In the embodiment of the invention of FIG. 1, a scanned charge-coupled-device (CCD), which is a planar array of light sensitive elements having a temporary charge storage characteristic, could be used instead of the vidicon tube 25.

In the embodiment of the invention of FIG. 1, a high capacity digital memory with an input analog-to-digital converter could be used instead of the electrical recording cathode ray tube 29. An input adder could add the input image point digital values to the contents of the corresponding memory cell, for each fan pattern, in a high speed memory scanning fashion. A high speed digital-to-analog converter could be used to scan readout the memory to television monitor 31.

In the embodiment of the invention of FIG. 1, a long-term integrating storage-type light-sensitive return beam vidicon (RBV) could be used instead of the temporary storage type vidicon 25 and the electrical recording storage cathode ray tube 29. The RBV face target would be disposed in the image plane 37. The RBV stored image can be read out for long periods. The scanning electron beam senses the target charge and is returned to a high gain electron multiplier adjacent to the electron beam gun. After amplification, the video output signal may be displayed on the television monitor CRT 31.

In the embodiment of the invention of FIG. 1, a permanent recording for later playback of the light beam signal linear projection attenuation profiles of the object cross-section that impinge on lens 13 could be made during real time cross-section image reconstruction by partially reflecting the laser scanning beam with a partial mirror to expose a photographic film. The partial mirror would be disposed in front of deflector 11 and at a 45 degree angle to the main optical axis. The photographic film would be disposed equi-distant from the partial mirror as lens 13. The film would be re-positioned after each x-ray detector sequence so as to record each light intensity profile. After processing the film as a positive transparency, the film could be positioned in front of lens 13 to modulate the scanning laser beam intensity while automatically generated control signals sequenced the system for laser beam scanning and image reconstruction.

Referring to FIG. 7, there is shown one method of correction for the superfluous spread distribution in the reconstructed cross-section image of the embodiment of the invention shown in FIG. 1. In this method a first sequence of x-ray detector signals is passed through a differentiating correction network of the type shown in FIG. 7A and simultaneously loaded into the shift register 55. A positive dc bias is added to the network input. The output of the network with a dc bias, modulates the laser beam intensity for a first scan. The first sequence image lines formed are temporarily stored on the vidicon target 37. The contents of the shift register is then brought out in a reverse second sequence into the differentiating network, while the laser beam is scanned in the reverse direction from control signal unit 56, deflecting the reverse differentiated x-ray detector signals to scan angles having correspondence with the first sequence. The second sequence of image lines are formed on the vidicon target, integrated, and temporarily stored with the first stored sequence for the particular x-ray beam fan pattern rotational angle. The stored corrected fan pattern of image lines is then destructively read out with the television-type raster scan for transferral to the long-term integrating storage cathode ray tube 29. This is repeated for each x-ray beam fan pattern pulsed over a 180 degrees rotational angle, forming a final reconstructed cross-section image corrected for superfluous spreads. In the correction network of FIG. 7A, shown with a basic rectangular profile x-ray detector signal time-sequenced input, capacitor C charges proportional to the size and attenuation of the object during the object's profile time duration and discharges its charge with opposite polarity into the following adjacent x-ray beam detector signal locations. In this manner the network generates correction amplitude spread and extent as a function of the object's size and attenuation, and symmetrically, for full correction around each cross-section object. The image line intensity profile stored is effectively the sum of the rectangular profile and an inverted polarity gaussian-type profile. Separately or combined, the gaussian-type profile integrates during correlation and integration to a like gaussian-type distribution having no superfluous spread distribution. The inverted gaussian-type distribution opposes and integrates, on the storage target of CRT 29, with the gaussian-type superfluous spread component of object correlation and integration, to a constant amplitude distribution upon which is superposed the corrected object image cylindrical distribution of reconstruction. An alternate method of correction in the invention to the said reversed second sequencing is to use a network of FIG. 7A to differentiate the normal x-ray detector signal sequences for 360 degrees rotation of the pulsed x-ray beam fan pattern, which effectively provides the reversed sequence profile for the said symmetrical correction around each object in the object cross-section layer. The correction network of FIG. 7A is an example which illustrates the principle of correction in this embodiment of the invention wherein the contents of the time-sequenced attenuation profile of an object is electrically sensed and is utilized in an electrical circuit to generate wave forms for proportional correction in the region surrounding the object reconstruction image. Those skilled in the art will of course appreciate that the network of 7A is given as an example of the principle of correction in the present embodiment of the invention and that additional components could be used in the network to optimize the match of the correction waveform to minimize the final superfluous spread distribution, and also that other equivalent analog or digital circuits could be used for the same effect.

Referring to FIG. 2, there is shown another embodiment of the electrode-optical signal correlator and integrator section of the embodiment of the invention of FIG. 1. In FIG. 2 means are included for correcting the superfluous object shadow spread in the reconstructed object cross-section. The operation of the system is similar to the system of FIG. 1. The sequence of x-ray detector signals from amplifier 8 for each x-ray beam fan pattern is stored and recirculated in shift register 55 during intensity modulation and scan of the laser beam. The recirculated x-ray detector signals are polarity inverted and sequenced to modulate the laser beam for a second fast scan. The second laser beam scan is deflected from the point above the first deflection point so as to like generate light beam signals through the optical system in the plane parallel and adjacent to the first plane of light beam signals. The second laser beam scan forms an inverted polarity light beam intensity linear projection object attenuated profile at lens 13. The normal polarity first intensity profile and the inverted polarity second intensity profile for an x-ray opaque cylindrical object volume in the object cross-section are shown adjacent to lens 13. A second negative cylindrical lens 22 is supported adjacent to the first lens 22 and like intercepts and diverges inverted polarity plane of light beam signals. The like parallel planes of diverged light ray signals from the second lens 22 are coplanar with those from the first lens 22 resulting in an inverted polarity fan pattern of image line signals in register with the normal polarity fan pattern of image line signals. A light dispersing filter 12, such as a finely textured glass plate, or an energized liquid crystal cell (LCC) of the dynamic scattering type, is disposed to intercept the inverted polarity light beam signals in front of the second lens 22. As shown in FIG. 2A the forward light dispersing pattern of filter 12 for an input light beam has a maximum intensity on axis and decreases in intensity gaussian-like for increasing off-axis angles. The inverted polarity light beam intensity profile for an object is dispersed by light filter 12 effectively into adjacent image signal lines forming an inverted polarity gaussian profile image signal strip. The dispersed light intensity in the image plan adjacent to the image signal strip is the integrated sum of dispersed light from the number of inverted polarity light beam signals dispersed by filter 12, causing the correcting inverting gaussian shape to increase in intensity amplitude and width as the object size increases. This provides correction proportional to the superfluous spread distribution of image correlation and integration. The inverted gaussian shaped image signal strip intensity profile is correlated and integrated having a like gaussian-type shape distribution with no superfluous spread, providing controlled correction of the reconstruction cross-section image. There is shown in FIG. 2, adjacent to the image plane 37, the intensity profile distribution of the sum of the normal profile and inverted polarity profile image line signals for an x-ray opaque cylindrical object volume which are in actuality sequentially generated and temporarily stored on the light sensitive vidicon 25. The correlated and corrected image fan patterns are read out and integrated on the storage target of the electrical recording cathode ray tube 29, forming a corrected image reconstruction charge amplitude distribution superposed on a constant amplitude charge distribution.

Referring to FIG. 3, there is shown another embodiment of the image plane sensing and integrating section of the embodiment of the invention of FIG. 1, wherein another means is utilized in the invention for generating the gaussian-shaped distribution correction of the aforementioned superfluous spread amplitude distribution of correlation and integration. This method utilizes a single sequence of x-ray detector signals from each x-ray beam fan pattern generated. A partial mirror 39 partially reflects the fan patterns of image line signals for correction to a second like vidicon 25. A light dispersing filter 12 is disposed in front of the target 37 of the second vidicon. Filter 12 is a finely textured glass plate or a liquid crystal cell (LCC) of the dynamic scattering type when energized. As shown in FIG. 3A, filter 12 has a forward light dispersing directional pattern which causes a gaussian-shaped intensity distribution on target 37. The television-type raster scan of the correcting image is reversed and positioned so as to read out the reversed mirror image in electrical register with the normal image on vidicon 25. The temporarily stored fan pattern images are read out from both vidicons in synchronism. The correcting vidicon output of the second vidicon 25 is polarity inverted by amplifier 41 and summed with the normal polarity video output of the first vidicon 25 in summing amplifier 40 and transmitted to the electrical recording storage cathode ray tube 29 which is raster-scanned in synchronism.

Referring to FIG. 4, there is shown a sequence of seven diagrams which can be used to facilitate the explanation of the principle of correlation and integration of the invention with a light beam analog of the x-ray beams. The input parallel light beams represent x-ray beams from a distant x-ray point source. In the diagram at the bottom of FIG. 4, light-attenuating point P on a transparent rotating Table 38 represents an object cross-section. A line DE represents the analogous location of x-ray beam detectors. The attenuated light beam signal is diverged uniformly by fixed negative cylindrical lens 22 depositing the value of the signal at all points equally at all possible location points along the line on target 37 of cathode ray tube 25. Table 38 and cathode ray tube 25 are rotated by equal angles $\theta$. Target 37 is a light sensitive dielectric charge integrating and storage target which can be charge-amplitude read out by a television-type raster scan of the cathode ray tube electron beam. The first diagram at the top of FIG. 4 is a plan view of the table 38 and lens 22 and the target 37 image turned sideways for clarification. In the sequence of plan view diagrams angle $\theta$ is sequenced in 30 degree increments, for simplification, moving point P to six positions. In the diagram a light beam is attenuated by point P producing a light beam signal to line DE at a point distant OA from the axis IJ, and diverged and deposited on target 37 as an image line signal of charge FG. In the second diagram table 38 and target 37 have rotated to angle $\theta$ equal to 30 degrees, and point P causes a light beam signal through line DE a distance OA, which is equal to $r\cos\theta$, and is deposited on the rotated target 37 distant $r\cos\theta$ from the axis of rotation. This sequence is continued until six image line signals have been recorded as signal charge lines on target 37. The point P attenuation value has been recorded as charge at all possible points on the six signal charge lines and correlated to a point P by intersection of the lines. The storage target integrates the charge at the correlation point P to a value six times greater than any other non-correlated line points. Continued rotation to 180 degrees would cause a redundant signal charge line coincident with first recorded line FG. From this series of diagrams it can be seen that x-ray detectors along line DE could be replaced with light beam signals intensity modulated proportional to the x-ray beam attenuation of the point P in an object cross-section 38.

Referring to FIG. 4A there is shown a diagram illustrating how the correlation of point P can be accomplished on the fixed target 37 as an extension of the explanation of FIG. 4. The linear projected distance OA of point P on analagous x-ray detector line DE is plotted on target 37 as distance OA to a line drawn parallel to line JC at angle $\theta$. Such lines drawn distances OA and parallel to rotating line JC, for the six positions at point P, all intersect at a fixed point P of correlation on target 37.

Referring to FIG. 4B, there is shown a side view of line DE, a rotatable dove prism 15 and lens 22, and a fixed cathode ray tube 25, used to obtain the correlation points previously described in FIG. 4A in accordance with the principles of the invention. Line DE represents the line of light beam signals as previously shown in FIG. 4B. Dove prism 15 is rotatable about its longitudinal axis of image rotation. Negative cylindrical lens 22 is rotary coupled to prism 15 through a one-to-two shaft angle ratio coupler. Cathode ray tube target 37 is a light sensitive dielectric charge integrating and storage target. Dove prism 15 performs the function of displacing and effectively rotating the plane of parallel light beam signals through line DE by angle $\theta$. Lens 22 diverges uniformly the rotated light beam signals to impinge on target 37 with equal signal intensity along the corresponding image signal lines. For the six positions of point P shown in FIG. 4A, six signal lines of charge are deposited on sixth target 37 intersecting and forming a correlation point for point P. The charge integrates at the correlation point to six times the amplitude at all other non-correlated signal line points as shown in FIG. 4C.

Referring to FIGS. 5, 5A, 5B and 5C, there is shown a side view, end view, rotated end view, and image line rotation, respectively in connection with functioning of the dove prism 15 of the invention. In FIG. 5, a light beam impinging on the prism at point Z is refracted internally to the bottom where it is reflected to exit at Z'. The refractive index and dimensions of the prism determine the optical axis of image rotation ZZ'. There is usually a mirror coating applied externally on the bottom surface of the dove prism. In the invention the axis ZZ' is coincident with the main optical system axis. In FIG. 5B, the solid line prism end view outline is shown at angle $\theta$ equal to zero degrees and the dotted outline is prism rotation to angle one-half $\theta$. An on-axis light beam enters prism at Z, is refracted to a point on line X at the bottom, reflected to Z' and exits the prism refracted on axis. Input light beam Y which is parallel to the prism axis is refracted to line X and exits at Y' at an equal distance from the prism axis. Prism 15 is then rotated to an angle equal to one-half $\theta$. On-axis input light beam Z is again refracted to the prism bottom and again exits on-axis. Input light beam Y enters the rotated prism, is refracted to the bottom at a point on line V and exits at Y''', an equal distance above line RS. The input light beam at Y has been rotated by angle $\theta$ with respect to light beam Z, which is twice the angle of prism rotation. In FIG. 5C, Y and Q are input parallel light beams in the plane of prism axis Z and parallel to the prism bottom. Lines IY and IQ represent image lines formed by the negative cylindrical lens 22 shown in FIG. 4B. For the prism rotation of one-half $\theta$, image lines IY prime and IQ prime have been constructed for rotated light beams Y prime and Q prime. The input light beams are always refracted directly to the prism bottom, and reflected to exit at an equal distance to prism plane RS of FIG. 5B. Thus a plane of input parallel light beams through the prism axis is displaced and effectively rotated by twice the angle of the prism rotation.

Referring to FIG. 6, there is shown a sequence of diagrams to facilitate an explanation of the correlation of x-ray beams in a fan pattern according to the principles of the invention. Light beams are fanning out from the point B analogously to the fan of x-ray beams from a point source. The light beams are in the plane of circular disk 38, analogous to an object cross-section layer, and impinge on line DE, analogous to the linear projection of a fan of x-ray beams through a cross-section layer to a line. All light beams arriving at line DE are extended as lines to point C, distance OC being equal to distance OB. Circular disk 38 contains a light attenuation point P and rotates about I counterclockwise. Circular disk 37 rotates clockwise about point J. Distance OI equals distance OJ. In the first diagram, point P attenuates a light beam at angle $\phi$ which intersects line DE a distance OA from point O. A line is drawn from point A, to point C forming line segment FG on disk 37. In the second diagram, both disks have been rotated by angle $\theta$. A light beam attentuated by point P at angle $\phi$ arrives at line DE a distance OH from point O. A line is drawn from point H to point C forming a second line segment on rotated disk 37. This process is continued for six positions of point P resulting in six line segments on disk 37 which all intersect at a common point which is the correlation point at point P on disk 37. If disk 37 is a hypothetical integrating storage disk and the line segments are drawn with intensity proportional to the attenuation then at the correlation point the intensity would be six times that of any other non-correlated points on the line segments.

Referring to 6A, there is shown the extension of the construction of FIG. 6 applied to a fixed non-rotating circular disk 37, in accordance with the principles of the invention. For the first position of point P at angle $\theta$ equal to zero, fan CDE is drawn, as previously for FIG. 6 forming line segment FG on disk 37. Fan CDE can rotate counter-clockwise about point J, and as shown with point C at angle $\theta$ of zero degrees. Disk 38 is rotated to angle $\theta$ and fan CDE is also rotated by angle $\theta$. Distance OH is marked off on line DE of rotated fan CDE and a line drawn from H to C forming a second line segment on fixed disk 37. This process is repeated for six positions of P forming six line segments intersecting and correlating point P to a fixed point on disk 37. In a like manner, each point in disk 38 may be correlated to a geometrically corresponding point on fixed disk 37. If disk 37 is a hypothetical integrating source and the line segments are drawn with intensity proportional to point P attenuation level at line DE, then at the correlation point the intensity would be six times that of any other non-correlated points on the line segments. In the invention, x-ray detectors detect the x-ray beam attenuation of an attenuating elemental volume in the cross-section intersecting an x-ray beam at angle $\phi$ with respect to an x-ray beam through the center of rotation of the fan of x-ray beams. The x-ray detector signal modulates a laser light beam at angle $\phi$ generating a light beam analog in a fan pattern as at the left side of FIG. 6A. Referring back to FIG. 1 of the invention, a positive cylindrical lens 13 is located corresponding to line DE of FIG. 6A and the fan of light beams are collimated as parallel light beam signals which are rotated by angle $\theta$ by the aforementioned dove prism 15. The light beam signals are then diverged by lens 22 and refracted by conical lens 23 to form the rotated fan pattern of image line signals on a light sensitive target corresponding to rotating fan of lines on the right side of FIG. 6A. FIG. 6B shows the fan pattern of image line charges on target 37.

Referring to FIG. 8, there is shown the development of the basic response of the system of the invention to a rectangular object attenuation profile signal. A rectangular attenuation profile signal at all fan beam angles is caused by an x-ray opaque cylindrical volume in the object cross-section layer and fully excites the system providing the full spatial frequency system response. As described previously, the scanning laser beam and rotating optical correlator of the invention, correlates each elemental object volume to a corresponding center of correlation in the image plane, where the elemental object attenuation signal intensity amplitude is placed at all possible points along the image line signal which are analogous to x-ray beam paths in the object cross-section. For a theoretical single object point, in an ideal system, image lines would intersect and correlate at a single point with no superfluous spread. For cross-section objects having real dimensions there is no clear 180 degree x-ray view of each object point since other object points cause interfering attenuation signals along an x-ray beam path. I have found experimentally that a simulated x-ray opaque cylindrical volume produces a system amplitude distribution of revolution as shown in FIG. 8B. For the present explanation the image line signals in the image plane of the invention are integrated as charge on the light sensitive storage target of a return beam vidicon in the image plane in accordance with the description of the invention. The explanation applies as well to the embodiment of the invention where a temporary storage device in the image plane stores and transfers each rotational fan pattern to a long-term integrating storage means, since integration by parts yields the same results. Shown in FIG. 8 is a rectangular profile charge strip signal of unit charge $C_u$ and width D corresponding to x-ray opaque cylindrical volume of diameter D and resulting from a corresponding intensity profile image strip signal.

As the x-ray fan beam rotates by delta $\theta$ ($\Delta\theta$) about a point in the object cross-section, charge strip signals $C_u$ are stored on the storage surface at delta $\theta$ increments about the center of correlation P. For one degree increments of delta $\theta$ and 179 total degrees of rotation, 179 unit charge strips would be formed as shown around point P. It can be seen that within a circle of diameter D, all charge strips will integrate defining the circle. For the particular scale of the figure, for explanatory purposes, the delta $\theta$ shown results in only approximately 12 unit charge strips over 179 degrees. FIG. 8A shows 12 units of charge for the center circle. In FIG. 8, at increasing radial distances it can be seen, with exaggeration, how this spatial correlation of the unit charge strip signal decreases. This is also shown in FIG. 8A, where the charge strips are drawn along the circumference at different radii, in a manner to show the total charge. In actuality the charge strips are on the storage surface. The dotted charge strips are those near the completion of 179 degrees and mesh with those at zero degrees to provide uniform charge level. For example at radius R = D there is four units overlap, at R = 2D there is two units overlap, at R = 3.5D there is no overlap and a constant one unit of charge. I have derived the equation expressing the charge amplitude distribution. In FIG. 8A, at radius R the total charge is the arc S divided by arc delta S, times unit charge $C_u$. As shown in FIG. 8, arc S = R times $\theta_D$, delta S = R times delta $\theta$, and $\theta_D$ is equal to two times the arc sine of D divided by 2R. Substituting these values as shown in the equation of FIG. 8A, the charge $C_r$ at any radius R is equal to the ratio of $2C_u$ to delta $\theta$, times the arc sine of D over 2R, where $\theta$ is in radians. As shown, the charge at any radius R with respect to the fully correlated charge $C_c$ at the center is equal to 2 over pi, times the arc sine of D over 2R. This equation is plotted in FIG. 8B which is the integrated charge distribution profile response about the x-ray opaque cylindrical volume of diameter D. It can be seen that the cylinder is sharply defined at the diameter, with at first a rapid decrease in charge to about half level followed by a gradually decreasing superfluous spread amplitude distribution of partially correlated charge strip signals.

Referring to FIG. 9, there is shown a series of input attenuation profile signals and reconstruction amplitude distributions which will assist in the understanding of x-ray cross-section image reconstruction according to the principles of the invention. FIG. 9A is an x-ray opaque cylindrical object volume which could be in an object cross-section layer. FIG. 9B illustrates the rectangular linear projection attenuation profile input signal generated and the resulting uncorrected superfluous spread amplitude distribution system response, in the integrating storage means. FIG. 9C is similar to 9B but is for a smaller diameter object volume. FIG. 9D illustrates the close approximation of the uncorrected system response to a cylindrical distribution superposed on a gaussian-type amplitude distribution. FIG. 9E is a cylindrical amplitude distribution obtained by graphically subtracting the gaussian distribution from FIG. 9D. FIG. 9F is the inverted gaussian-type correcting profile obtained by dispersion of the inverted polarity input profile signals with a gaussian-type light beam dispersing filter in accordance with the principles of the invention. FIG. 9G illustrates the like gaussian inverted amplitude distribution of correlation and integration formed in the storage means, and the normal uncorrected system response distribution. The integrated sum of these two distributions in the storage means is shown in FIG. 9H, being the corrected system response superposed on a predictable constant amplitude distribution level. FIG. 9I illustrates the integrated sum of a normal polarity charge strip profile and an inverted gaussian charge strip profile for an x-ray beam fan pattern rotational angle. This is illustrative of the principle of anticipating the superfluous spread distribution of correlation and integration with the inverted gaussian-type input profile signal.

FIG. 9J shows a typically uniform density cylindrical object volume which could be in a human object cross-section layer. A typical x-ray beam path through the object volume is shown. FIG. 9K is a plot of the x-ray beam path lengths in the object volume of FIG. 9J. For a uniform density object the x-ray beam attenuation is proportional to the path lengths and hence FIG. 9K is also the input attenuation profile signal obtained from the x-ray beam path attenuation detected signal amplitudes. This input profile signal is conveyed through the electro optical section of the invention and is the profile of the image line strip and charge signal strip in the integrating storage means in accordance with the principles of the invention. In FIG. 9L, I have shown how the object profile signal can theoretically be represented by constituent rectangular profile signals of varying widths and equal heights. It can be seen that a large enough number of rectangular profiles included would provide a complete representation of the object input profile. FIG. 9M illustrates the individual rectangular profile's superfluous spread distribution anticipated in accordance with the principles of the invention. In FIG. 9N, there is shown the integrated sum in the storage means of the individual uncorrected system responses of FIG. 9M. There is also shown, in FIG. 9N, a gaussian-type distribution drawn to closely follow the superfluous spread distribution and which could be substracted, or added, inverted, for spread correction. In FIG. 9O, there is shown the theoretical constituent rectangular profiles of FIG. 9L, polarity inverted and each having gaussian correcting dispersion according to the principles of the invention. In FIG. 9P there is shown the object's inverted polarity input profile, and the inverted gaussian-like correcting profile caused by the gaussian-like dispersing light filter in accordance with the principles of the invention and which theoretically could be represented by the intensity sum of the individual gaussian profiles of FIG. 9O. In FIG. 9Q, there is shown the inverted gaussian-like distribution in the storage means which is a result of the correlation and integration of the inverted gaussian-like profile of FIG. 9P, whereby each theoretical constituent gaussian-type input profile of FIG. 9O correlates and integrates to form like gaussian distributions in the storage means. If the parts are equal, then the sums of the parts are equal. That is, since a gaussian-type profile charge strip correlates and integrates rotationally about a correlation center with a like gaussian-type amplitude distribution, then the correction of the constituent rectangular profile provides correction for the whole object attenuation profile. FIG. 9R shows the corrected system response charge distribution, being the integrated sum of the uncorrected and correcting charge amplitude distributions of FIG. 9Q. The corrected distribution is superposed on a predictable constant amplitude distribution. FIG. 9S shows the charge strip signal profile stored for each x-ray fan beam rotational angle, being the integrated sum of the normal charge strip profile and an inverted polarity gaussian charge strip profile, illustrating the principle of anticipating the superfluous spread distribution of correlation and integration with the inverted gaussian profile.

Referring to FIGS. 12, 12A, 12B, and 12C, there is shown three different diameter uniform density objects which could be in a human object cross-section, and the extension of the analysis of FIG. 9 to this example.

In FIGS. 10 and 11, I illustrate my method of analysis which shows how an object in a cross-section layer has an x-ray attenuation profile which is the sum of constituent rectangular attentuation profiles, in accordance with the principles of the invention. The object in FIG. 10 is of uniform x-ray density and is a cylindrical object within the object cross-section layer. X-ray beams shown are at rotational angle $\theta$ and x-ray beam detectors measure the x-ray beam attenuations after passing through the object providing an object attenuation profile. The object cylinder is divided into equal thickness sections, delta Z. Each section has a constant x-ray attenuation proportional to delta Z, everywhere through its thickness and hence a rectangular attenuation profile. The section rectangular profiles of equal amplitude may be summed as in FIG. 11 to form the object attenuation profile which is the same as that measured by the x-ray detector. For the cylindrical object, the section rectangular profiles are seen at all rotational angles $\theta$. In accordance with the principles of the invention, the object attenuation profile signal is stored equally as a charge strip signal along the angle $\theta$, having the same object attenuation profile. The thoeretical constituent rectangular profile charge strips each correlate and integrate about the object's correlation center, each forming superfluous spread distribution, as described previously in the invention, and which integrate to form the total superfluous spread for the uniform density cylindrical object. In like manner the correcting inverted polarity object attenuation profile constituent rectangular attenuation profiles are gaussian dispersed as previously described for FIG. 9O forming constituent gaussian distribution, providing correction for each constituent rectangular profile and consequently full object reconstruction distribution correction, in accordance with the principles of the invention. In FIG. 11 the view of the constituent rectangular attenuation profiles, shown for one angle $\theta$, is the same for all angles $\theta$, therefore each constituent rectangular attenuation profile describes a circular locus of revolution, a cylinder, demonstrating that the uniform density cylindrical object attenuation distribution can be represented by a sufficiently large number of unit cylindrical distributions of various diameters as the section thickness delta Z is made arbitrarily small. Thus, I have shown that the sum of a number of rectangular attenuation profiles as in FIG. 11, describes the attenuation profiles of a corresponding number of cylindrical distributions which describes the attenuation distribution of a uniform density cylindrical object in the object cross-section. Furthermore, the entire object cross-section layer can be represented by such cylindrical volumes each of density present locally. The smallness of the elemental cylindrical volumes is limited to the resolution of the x-ray beam system.

Referring to FIG. 13, there is shown a simplified outline drawing of a typical cross-section image through the human skull showing the bone structure, nasal cavity, and eyeballs, and which I have generated as a cross-section image of reconstruction according to the principles of the invention.

While I have described the principles of my invention in connection with specific apparatus, it is to be clearly understood that this description is made only by way of example and not as a limitation to the scope of my invention as set forth in the accompanying claims.

I claim:

1. An x-ray object cross-section image reconstruction system comprising:

an x-ray apparatus projecting x-rays in a diverging fan, from a point source, through an object cross-section layer for a multiplicity of rotational angles of said point source with respect to a point in said cross-section; x-ray detection means disposed in the plane of said cross-section measuring the object cross-section path attenuations of x-ray beams fanning out at angular spacings within said fan, for each said fan rotational angle, said measurements being x-ray beam path attenuation signals, the total said rotation angle preferably being 180 degrees;

mean generating from a first fixed point, a light beam signal analog of said fan pattern of path attenuation x-ray beam signals, said light beam signals being in a first plane and having intensities determined by and analogous to said detected attenuated x-ray beam signals, said light beams generated in said fan patterns having angular spacing and beam widths analogous to and corresponding to said detected fan pattern of x-ray beams, said fan pattern of light beam signals being projected toward an image plane which is disposed perpendicularly to a central said fan light beam signal corresponding to a said x-ray beam passing through the said cross-section point of rotation, said light beam signal defines the optical axis to said image plane, said fan of light beam signals passing through a line perpendicular to said optical axis being a light beam signal intensity analog of the linear projection x-ray fan beam object attenuation profile for the corresponding said x-ray fan rotational angle, the present means generating a like second fan pattern of light beam signals having inverted polarity intensity signals and from a second fixed point which is adjacent to the said first fixed point, projecting in a plane parallel to said first fan pattern plane from said first fixed point and towards said image plane, being an image correcting fan pattern of light beam signals;

means collimating said light beam signals in said fan patterns, disposed at said perpendicular line, intercepting and directing said first and second fan patterns of light beam signals as parallel light beam signals in their respective said adjacent planes parallel to said optical axis and towards said image plane;

means intercepting and displacing said first and second planes of parallel light beam signals effectively rotating said planes about said optical axis to angles equal to said x-ray fan pattern rotational angles, said first plane being rotated about said optical axis, said adjacent inverted polarity light beam signals in said second plane being rotated about said optical axis with said adjacent relationship being constant;

means intercepting and diverging said displaced parallel light beam signals forming uniformly diverging light ray signals in parallel planes, said means having means intercepting said rotated first plane of parallel light beam signals forming first parallel planes of uniformly diverging light ray signals perpendicular to said first plane and toward said image plane, said means having means intercepting said second rotated planes of inverted polarity parallel light beam signals and like forming uniformly diverging inverted polarity light ray signals in second parallel planes towards said image planes, said first and second parallel planes of diverged light ray signals being coplanar;

means intercepting and imaging said light ray signals in said rotated coplanar parallel planes forming image line signals in a fan pattern in said image plane analogous to said x-ray beam fan pattern for each said x-ray fan rotational angle;

means dispersing light disposed in front of said means diverging said second plane of inverted polarity parallel light beam signals, said light disperser effectively intercepting and dispersing said light beam signals into neighboring said image line signals in said image plane, said light disperser having a light transmission directional characteristic forming strips of inverted polarity image line signals having an inverted polarity gaussian-shaped intensity distribution profile, said gaussian-shaped image strip profile increasing in intensity and amplitude and width as a function of the intensity and number of adjacent inverted polarity light beam signals contributing dispersed light, the light integral of adjacent gaussian-shaped dispersions being a like gaussian-shaped dispersion of increasing intensity and width proportional to said object size and density, said gaussian-shaped inverted polarity image strip signals being in register and colinear with said image line signals formed by said first plane parallel light beam signals said diverged into said coplanar parallel planes;

means sensing and storage integrating the light intensity of said fan patterns of image line signals for elemental points in said image plane, said elements of said means having geometric correspondence with said image plane elemental points, an elemental object volume in said object cross-section layer attenuating x-ray beams in said rotated fan pattern generating corresponding image line signals intersecting and defining the location of said elemental object in said image plane, being a center of spatial correlation, an x-ray opaque cylindrical volume in said object cross-section intercepting and attenuating a multiplicity of x-ray beams in said fan patterns generating corresponding strips of image line signals, in said first fan pattern, having rectangular intensity profiles intersecting at said center of spatial correlation, being said sensed and integrated for said elemental image plane points and having an amplitude distribution with a constant level circular area of amplitude equal to the integral sum of said intersecting rectangular profile image line signal strips, and radially thereafter the amplitude initially decreasing sharply followed by a gradual decreasing amplitude, proportional to the arc sine of the ratio of the object's radius to the said radial distance, being the basic uncorrected fully excited system response, said amplitude distribution being closely approximated as a cylindrical distribution superposed on a gaussian-shaped radially spreading distribution, said spread distribution being superfluous partial correlation and integration of image line signals of cross-section image reconstruction according to said arc sine function, having increasing superfluous spread amplitudes with said object size and density, said inverted polarity gaussian shaped intensity profile image line signal strips generated by said x-ray opaque cylindrical object volume being light sensed, correlated and integrated having an inverted gaussian shape amplitude distribution radially from said center of spatial correlation, said inverted gaussian shape distribution and said superfluous spread distribution integrating to a constant amplitude level having said cylindrical amplitude distribution superposed providing a corrected reconstruction attenuation amplitude distribution of said cylindrical object volume, uniform density elemental cylindrical object volumes represented by constituent cylindrical volumes having rectangular attenuation profiles being like corrected, typical human cross-section layer having various size and shape objects and of various densities which could be represented by constituent said uniform density cylindrical volumes, attenuating said x-ray beam fan patterns, generate corresponding said image line signals and said inverted polarity correcting image line gaussian shape profile signals, forming said amplitude distributions like corrected for superfluous spread amplitude distribution;

means for displaying said stored amplitude distribution of said spatial correlation and integration for said elemental object image points in the storage means of said mean sensing and storage integrating, said display having geometrical correspondence with said object image plane points.

2. The system of claim 1 wherein:

said means generating light beam analogs of said fan patterns of attenuated x-ray beam signals is a laser light beam scanner, deflected and beam intensity modulated by said x-ray detector signals generating said analog fan patterns of light beam signals from said fixed points and through said perpendicular lines; and said means collimating said light beam fan patterns is a positive cylindrical lens; and said means intercepting and displacing said parallel light beam signals is a refracting and reflecting dove prism having its axis of image rotation coincident with said optical axis and being rotated about said axis to said angles equal to one-half of said rotational angles, said dove prism inherently causing two times output light beam signal rotation; and said means intercepting and uniformly diverging said first and second parallel light beam signals is comprised of a negative cylindrical lens disposed in each said rotated first and second planes of parallel light beams, said negative lens being coupled to said rotated dove prism to rotate in the same direction and to two times the rotation angle of said dove prism; and said means intercepting and imaging said rotated coplanar parallel planes of light ray signals is a conical type lens refracting and imaging said light planes to form said fan patterns of image lines in said image plane, said conical type lens being coupled to said negative cylindrical lens for rotation in unison.

3. The system of claim 2 wherein:

said means sensing and storage integrating is comprised of a planar array of photo-sensitive integrating storage elements disposed in said image plane having means operating said array providing electrical output signals conveying the integrated and stored photosensitive element amplitude responses to geometrically corresponding points in said display means.

4. The system of claim 2 wherein:

said means sensing and storage integrating is comprised of a planar array of photo-sensitive elements having a temporary integrating storage characteristic sensing and storing each set image line signal fan pattern, said elements being scanned and said fan patterns of image line signal intensities being transmitted as electrical amplitudes to a long-term said integrating storage means having elemental storage points with correspondence to said photosensitive elements.

5. The system of claim 4 wherein:

said planar array of photo-sensitive elements having means for scanning in a television-type sequence during said signal transmittal to said storage means, said sequence being synchronized and occurring for each said x-ray beam fan pattern rotational angle; and said x-ray beam detector signals for each said fan pattern rotational angle are momentarily stored and sequentially sampled a first and a second time during the retrace time period of said television-type scan; and said laser beam scanner having means for beam intensity modulation by said first time sampled signal sequence and having means for deflection from said first fixed point to angles equal to said angular spacings of said x-ray beams within said fan pattern, in like manner generating said inverted polarity light beam signals said laser beam is scanned from said second fixed point with said stored detector signals during said second sampling time; and said image line signal fan pattern intensities generated in said image plane during said first sampling time being sensed and temporarily stored electrically in said planar array of photo-sensitive elements, said fan patterns of image line signals having inverted polarity gaussian shaped dispersions being generated during said second sampling time being integrated and summed with said first sampling time intensities stored in said photo sensitive means, followed by readout said television-type scans of said photo sensitive elements, transmitting said summed image line signal fan patterns elemental electrical amplitudes to said long-term integrating storage means.

6. The system of claim 5 wherein:

said long-term integrating storage means is a semiconductor digital storage memory wherein said television-type scan signal amplitudes from said photo-sensitive array elements are quantized as digital values and digitally added to the digital contents of corresponding said memory storage elements, means being provided for addressing said memory element contents for retrieval and digital-to-analog conversion and transmission to said display means.

7. The system of claim 5 wherein:

said long-term integrating storage means is a storage type cathode ray tube having an electron beam scan electrical charge integrating storage target, said electron beam being intensity modulated by said television-type scan readout signal amplitudes and deflected to scan said storage target in synchronism with said television-type scan, addressing and charge storage integrating at elemental target storage points, said storage cathode ray tube target charge amplitude distribution modulating a television-type scan charge readout electron beam providing an output signal measure of said charge distribution for display by said display means.

8. The system of claim 2 wherein:

said means dispersing light is a liquid crystal cell of the light scattering type said disposed and having its alternating excitation voltage adjustable for optimum correcting said gaussian shape type dispersion.

9. The system of claim 2 wherein:

said means dispersing light is a transparent sheet having a fine randomly textured surface providing said gaussian shaped light dispersion characteristics.

10. The system of claim 3 wherein:

said means sensing and storage integrating is a light input storage cathode ray tube such as a return beam vidicon having a target comprised of photosensitive elements responsive to the integral of light intensity and providing long-term electron beam television-type readout of said stored amplitude distribution to said display means.

11. The system of claim 7 wherein:

said display means is a television-type cathode ray tube monitor operating in synchronism with said readout scan and displaying said charge amplitude distribution as shades of gray, being said reconstructed x-ray image of said object cross-section.

12. An x-ray object cross-section image reconstruction system comprising:

an x-ray apparatus projecting x-rays in a diverging fan from a point source and through an object cross-section layer for a multiplicity of rotational angles of said point source with respect to a point in said cross-section, x-ray detection means disposed in the plane of said cross-section measuring path attenuations of x-ray beams fanning out at angular spacings within said fan and for each said rotational angle, said detected attenuated x-ray beams being in a fan pattern at said rotational angles, said path attenuation measurements being x-ray beam path attenuation signals for said x-ray beams in said rotational fan pattern, the total said rotation preferably being 180 degrees;

means generating, from a fixed point, light beam signal analog of said fan patterns of path attenuated x-ray beam signals, said light beam signals being in a plane and having intensities determined by and analogous to said x-ray beam attenuation signals, said light beams generated having corresponding said x-ray beams angular spacings and analogous widths, said fan pattern of light beam signals being projected toward a first image plane disposed perpendicularly to the central light beam, the central light beam signal corresponding to the central said x-ray beam passing through said point of rotation in said object cross-section defining the optical axis to said first image plane, said fan pattern of light beam signals intersecting a line perpendicular to said optical axis being the light beam signal intensity analog of the linear projection x-ray beam object attenuation profile for each said x-ray fan pattern rotational angle;

means collimating said light beam signals in said fan pattern, disposed at said perpendicular line, intercepting and directing said light beam signals as parallel light beam signals, in said plane, parallel to said optical axis and toward said first image plane;

means intercepting and displacing said plane of parallel light beam signals effectively rotating said plane about said optical axis to angles equal to said x-ray fan pattern rotational angles;

means intercepting and diverging said displaced parallel light beam signals forming uniformly diverging light ray signals in parallel planes, said parallel planes of said light ray signals being perpendicular to said rotated plane and diverging towards said first image plane;

means intercepting and imaging said light ray signals in said rotated parallel planes forming image line signals in a fan pattern in said first image plane analogous to said rotated x-ray beam fan pattern, an elemental object volume in said object cross-section layer attenuating x-ray beams in said rotated fan patterns generating image line signals intersecting and defining the location of said elemental objects in said image plane, being centers of spatial correlation having a one-to-one geometric correspondence with said object cross-section;

means partially intercepting and directing said light ray signals forming said fan patterns of image line signals toward a second image plane forming like said fan patterns;

means dispersing light disposed in front of said second image plane intercepting and dispersing said light ray signals into neighboring image line signals in said second image planes forming correcting image line signals, said light disperser having a transmission characteristic forming image line signals having a gaussian-shaped intensity distribution image line profile, said gaussian-shaped profile increasing in intensity amplitude and width as a function of the number of adjacent image line light ray signals contributing dispersed light, the light integral of said adjacent gaussian-shaped dispersion being a like gaussian-shaped dispersion of increasing intensity and width, an elemental object volume in said object cross-section layer attenuating x-ray beams in said rotated fan patterns generating said correcting image line signals intersecting and defining the locations of said elemental objects in said second image plane, being centers of spatial correlation having a one-to-one geometrical correspondence with said object cross-section;

means sensing and converting to electrical amplitude signals the light intensity of said fan patterns of image line signals at elemental points in said first image plane, the elements of said means having geometric correspondence with said image plane elemental points;

means sensing and converting to electrical amplitude signals the light intensity of said fan patterns of said correcting image line signals at elemental points in said second image planes, the elements of said means having a geometrical correspondence to said image plane elemental points;

means receiving and inverting the polarity of said correcting image line electrical signals;

means receiving and storage integrating in elemental storage means the electrical signals from said first image plane sensing means and from said means inverting polarity for each corresponding said cross-section elemental object volume, said elemental storage means having a one-to-one correspondence with said object cross-section and said first and second image plane elemental points, an x-ray opaque cylindrical volume in said object cross-section intercepting and attenuating a multiplicity of x-ray beams in said rotated fan patterns generating corresponding strips of image line signals in said first image plane having rectangular intensity profiles intersecting and overlapping at said center of spatial correlation, being said sensed and converted to electrical signals and said integrated for said elemental points in said first image plane, having an amplitude distribution of constant level circular area of amplitude equal to the integral of said intersecting rectangular profile strips, and radially thereafter the amplitude initially decreasing sharply followed by a gradual decreasing amplitude proportional to the arc sine of the ratio of the object radius to the said radial distance, being the basic uncorrected fully excited system response, said amplitude distribution being closely approximated as a cylindrical distribution superposed on a gaussian-shaped spreading distribution, said spread distribution being superfluous image line signal partial correlation and integration of cross-section image reconstruction following said arc sine function with increasing superfluous spread amplitude with object size and density, said correcting image line signals forming said gaussian-shaped intensity profile strips in said second image plane generated by said x-ray opaque cylindrical object volume and said sensed and converted to inverted polarity correcting electrical signals being like integrated in said storage elements, this integration having an inverted gaussian amplitude distribution radially from said center of spatial correlation, said inverted gaussian-shaped distribution and said superfluous spread distribution integrating to a constant amplitude level having said cylindrical amplitude distribution superposed providing a corrected reconstruction attenuation amplitude distribution of said cylindrical object volume, uniform density elemental cylindrical object volumes represented by constituent cylindrical volumes having rectangular attenuation profiles being like corrected, typical human cross-section layers having various size and shape objects of various densities which could be represented by constituent said uniform density cylindrical volumes attenuating said x-ray beam fan patterns, generate corresponding image line electrical signals and said inverted polarity correcting gaussian-shaped profile image line electrical signals being like corrected for superfluous spread amplitude distributions;

means for displaying the stored amplitude distribution of said spatial correlation and integration for said elemental object image points in said storage means, said display having geometrical correspondence with said object image plane points.

13. The system of claim 12 wherein:

said means generating light beam analogs of said fan patterns of attenuated x-ray beam signals is a laser light beam scanner, deflected and beam intensity modulated proportional to said x-ray detector attenuation signals, generating said fan patterns of light beam signals from said fixed point and through said perpendicular lines; and said means collimating said light beam fan patterns is a positive cylindrical lens disposed at said perpendicular line; and said means intercepting and displacing said parallel light beam signals is a light refracting and reflecting dove prism having its axis of image rotation coincident with said optical axis and being rotated about said axis to angles equal to one-half of said x-ray beam fan pattern rotational angles, said dove prism inherently having two times output light beam rotation; and said means intercepting and diverging said parallel light beam signals is a negative cylindrical lens, said negative lens being coupled to said rotated dove prism and rotated in the same direction to two times the rotation angle of said dove prism; and said means intercepting and imaging said rotated parallel planes of light ray signals is a conical type lens refracting and imaging said light planes to form said fan patterns of image line signals in said first and said second image planes, said conical type lens is coupled to said negative cylindrical lens for rotation in unison; and said means partially intercepting and directing light rays to said second image plane is a partial mirror beam splitter disposed at 45 degrees to said optical axis reflecting said light rays to said second image plane beam perpendicular to the reflected said optical axis and equidistant to the said first image plane.

14. The system of claim 13 wherein:

said means sensing and converting to electrical amplitude signals light intensities at elemental points in said first plane is comprised of a planar array of photo-sensitive elements having a temporary integrating storage characteristic, sensing and temporarily storing each said image line signal fan pattern, said photo-sensitive element signals for each said fan pattern being scanned and read out in television-type sequence, amplified, and transmitted to said means receiving and storage integrating; and said means sensing and converting to electrical amplitude signals light intensity at elemental points in said second image plane is comprised of a like planar array of photo-sensitive elements like scanned and amplified, the present scan sequence being reversed, reading out signals from the reversed image reflected from said partial mirror beam splitter in effective electrical register with said scan sequence of said first image plane planar array, said amplified readout correcting signals being transmitted to said means inverting signal polarity; and said means receiving and inverting the polarity of said correcting image line electrical signals is a polarity inverting electrical signal amplifier.

15. The system of claim 14 wherein:

said first and second planar arrays of photo-sensitive elements scanned in said television-type element sequence being synchronized and occurring for each said x-ray beam fan pattern rotational angle; and said x-ray detector signals for each said fan pattern rotational angle are momentarily stored and sequentially sampled during the retrace time period of said television-type scan; and said laser beam scanner having means for beam intensity modulation by said sampled detector signal sequence and having means for beam deflection from said fixed point equal to said angular spacings of said x-ray beams within said fan pattern; and said image line signal intensities generated in said first and second image planes during said sampling sequence being said sensed and temporarily stored electrically in said planar arrays of photo-sensitive elements, followed by synchronized television-type scan readouts of said photo-sensitive elements transmitting electrical amplitude signals of said photo-sensitive elements to said storage integrating means and to said signal polarity inverting amplifier respectively.

16. The system of claim 15 wherein:

said means receiving and storage integrating is a semiconductor digital storage memory having elemental storage means, said electrical amplitude signals received from said first image plane photo-sensitive array and from said signal polarity inverting amplifier being quantized as digital values and digitally added to the digital contents of corresponding said memory storage elements, means being provided for addressing said memory element contents for retrieval and digital-to-analog conversion and transmission to said display means.

17. The system of claim 15 wherein:

said means receiving and storage integrating is a storage type cathode ray tube having an electron beam scan electrical charge integrating storage target, said electron beam being intensity modulated by said television-type scan readout signal amplitudes and deflected to scan said storage target in synchronism with said television readout scan, addressing and storage integrating at corresponding elemental target storage points, said storage cathode ray tube target charge amplitude distribution modulating a television-type scan charge readout electron beam providing an output signal measure of said charge distributions for transmission to and display by said display means.

18. The system of claim 13 wherein:

said means dispersing light is a liquid crystal cell of the light scattering type, said disposed and having its alternating excitation voltage adjustable for optimum correcting said gaussian-shaped dispersion.

19. The system of claim 13 wherein:

said means dispersing light is a transparent sheet having a fine randomly textured surface providing said gaussian-shaped type light dispersion.

20. The system of claim 17 wherein:

said display means is a television-type cathode ray tube monitor operating in synchronism with said readout scan and displaying said charge amplitude distributions as shades of gray, being said reconstructed x-ray image of said object cross-section.

21. The system of claim 15 wherein:
each said planar array of photo-sensitive elements is the photo-sensitive target plane at the face plate of a vidicon type television camera cathode ray tube, said vidicon providing said temporary storage of each said sequence of fan patterns of image line signals for said television-type readout scan.

22. The system of claim 15 wherein:
each said planar array of photo-sensitive elements is a charge-coupled-device (CCD) array, providing said temporary storage of each said sequence of fan patterns of image line signals and operated with said television-type readout scan.

23. The system of claim 13 wherein:
said laser scanner generating light beams signal analogs of said fan patterns of attenuated x-ray beam signals includes partial reflective means for recording during reconstruction for later playback, a photographic film record of said x-ray detector signals forming said light intensity linear projection attenuation profiles disposed at said perpendicular line for said fan pattern rotational angles, said film record, after processing, being disposed at said perpendicular line, providing a playback said laser beam intensity modulation proportional to said x-ray detector attenuation signals for cross-section image reconstruction.

24. The system of claim 17 wherein:
said means receiving and storage integrating includes an input summing amplifier receiving said synchronous readout signals of said elements in said first image plane photo-sensitive array and said inverted polarity signal from elements in said second image plane photo sensitive array, for each corresponding image elements said summing amplifier outputs the instantaneous sum of said signals for said modulation of said electron beams.

25. An x-ray object cross-section image reconstruction system comprising:
an x-ray apparatus projecting x-rays in a diverging fan from a point source and through an object cross-section layer for a multiplicity of rotational angles of said point source with respect to a point in said cross-section, x-ray detection means disposed in the plane of said cross-section measuring path attenuations of x-ray beams fanning out at angular spacings within said fan and for each said rotational angle, said detected attenuated x-ray beams being in a fan pattern at said rotational angles, said path attenuation measurements being x-ray beam path attenuation signals for said x-ray beams in said rotational fan pattern, the total said rotation preferably being 180 degrees;
means generating, from a fixed point, light beam signal analogs of said fan pattern of path attenuated x-ray beam signals, said light beam signals being in a plane and having intensities determined by and analogous to said x-ray beam attenuation signals, said light beams generated having corresponding said x-ray beams angular spacings and analogous beam widths, said fan pattern of light beam signals being projected towards an image plane disposed perpendicularly to the central light beam, the central light beam signal corresponding to the central said x-ray beam passing through said point of rotation and in said object cross-section defining the optical axis to said image plane, said fan pattern of light beam signals intersecting a line perpendicular to said optical axis being the light beam signal intensity analog of the linear projection x-ray beam object attenuation profile for each said x-ray fan pattern rotational angle;
means collimating said light beam signals in said fan pattern, disposed at said perpendicular line, intercepting and directing said light beam signals, in said plane, parallel to said optical axis and toward said image plane;
means intercepting and displacing said plane of parallel light beam signals effectively rotating said plane about said optical axis to angles equal to said x-ray fan pattern rotational angles;
means intercepting and diverging said displaced parallel light beam signals forming uniformly diverging light ray signals in parallel planes; said parallel planes being perpendicular to said rotated plane and diverging towards said image plane;
means intercepting and imaging said light ray signals in said rotated parallel planes forming image line signals in a fan pattern in said image plane analogous to said rotated x-ray beam fan patterns, an elemental object volume in said object cross-section layer attenuating x-ray beams in said rotated fan pattern generating image line signals intersecting and defining the location of said elemental objects in said image plane, being the center of spatial correlation having a one-to-one geometrical correspondence with said object cross-section;
means sensing and storage integrating the light intensity of said fan patterns of image line signals for elemental points in said image plane, said elements of said means having geometrical correspondence with said image plane elemental points, an x-ray opaque cylindrical volume in said object cross-section intercepting and attenuating a multiplicity of x-ray beams in said fan patterns generating corresponding strips of image line signals, in said fan pattern, having rectangular intensity profiles intersecting at said center of spatial correlation, being said sensed and integrated for said elemental image plane points and having an amplitude distribution of constant level circular area of amplitude equal to the integral of said intersecting image line signal strips, and radially thereafter the amplitude initially decreasing sharply followed by a gradual decreasing amplitude proportional to the arc sine of the ratio of the object radius to the said radial distance, being the basic uncorrected fully excited system response, said amplitude distribution being closely approximated as a cylindrical distribution superposed on a gaussian-shaped spreading distribution, said spread distribution being superfluous partial correlation and integration of said image line signal strips of cross-section image reconstruction following said arc sine function with increasing superfluous spread amplitude with object size and in density, uniform density elemental cylindrical object volumes represented by constituent cylindrical volumes having rectangular profiles having like superfluous spread distribution, typical human cross-section layers having various size and shape objects and of various densities which could be represented by constituent said uniform density cylindrical object volumes, attenuating said x-ray beam fan patterns generating corresponding image line signals being said reconstructed having said uncorrected superfluous spread amplitude distribution;

means for displaying said stored amplitude distribution of said spatial correlation and integration for said elemental object image points in the storage means of said light sensing and storage integrating, said display having geometrical correspondence with said object image plane points.

26. The system of claim 25 wherein:

said means generating light beam analogs of said fan patterns of attenuated x-ray beam signals is a laser beam scanner, deflected and beam intensity modulated proportional to said x-ray detector attenuation signals, generating said fan patterns of light beam signals from said fixed point and through said perpendicular line; and said means collimating said light beam fan patterns is a positive cylindrical lens disposed at said perpendicular line; and said means intercepting and displaing said parallel light beam signals is a light refracting and reflecting dove prism having its axis of image rotation coincident with said optical axis and being rotated about said axis to angles equal to one-half said x-ray beam fan pattern rotational angles, said dove prism inherently having two times output light beam rotation; and said means intercepting and diverging said parallel light beam signals is a negative cylindrical lens, said negative cylindrical lens being coupled to said rotated dove prism and rotated in the same direction to two times the rotation angle of said dove prism; and said means intercepting and imaging said rotated parallel planes of said light ray signals is a conical type lens refracting and imaging said light planes to form said fan patterns of image line signals in said image plane, said conical type lens being coupled to said negative cylindrical lens for rotation in unison.

27. The system of claim 26 wherein:

said means sensing and storage integrating is comprised of a planar array of photo-sensitive integrating storage elements disposed in said image plane and having means operating said array providing electrical output signals conveying the integrated and stored photo sensitive element amplitude responses to geometrically corresponding points in said display means.

28. The system of claim 26 wherein:

said means sensing and storage integrating is composed of a planar array of photo-sensitive elements having a temporary integrating storage characteristic sensing and storing electrically each said image line signal intensity fan pattern, said elements being scanned and said temporarily stored electrical signals being transmitted as electrical amplitudes to a long-term said integrating storage means having elemental storage points having correspondence to said photo-sensitive elements.

29. The system of claim 28 wherein:

said planar array of photo-sensitive elements having means for scanning in a television type sequence during said signal transmittal to said storage means, said sequence being synchronized and occurring for each said x-ray beam fan pattern rotational angle; and said x-ray beam detector signals for each fan pattern rotational angle are momentarily stored and sequentially sampled during the retrace time period of said television-type scan; and said laser beam scanner having means for beam intensity modulation by said sampled signal sequence and having means for deflection from said fixed point by said angular spacing of said x-ray beams within said fan pattern; and said image line signal fan pattern intensities generated in said image planes during said sampling pattern being sensed and temporarily stored electrically in said planar array photo-sensitive elements, followed by a readout said television-type scan of said photo sensitive element transmitting said image line signal fan pattern elemental electrical amplitudes to said long-term integrating storage means.

30. The system of claim 29 wherein:

said long-term integrating storage means is a semiconductor digital storage memory wherein said television-type scan signal amplitudes from said photo sensitive array elements are quantized as digital values and digitally added to the digital contents of corresponding said memory storage elements, means being provided for addressing said memory element contents for retrieval and digital-to-analog inversion and transmission to said display means.

31. The system of claim 29 wherein:

said long-term integrating storage means is a storage type cathode ray tube having an electron beam scan electrical charge integrating storage target, said electron beam being intensity modulated by said television-type scan readout signal amplitudes and deflected to scan said storage target in synchronism with said television-type scan, addressing and charge storage integrating at elemental target points, said storage cathode ray tube charge amplitude distribution modulating a television-type scan charge readout electron beam providing an output signal measure of said charge distributions for display by said display means.

32. The system of claim 27 wherein:

said means sensing and storage integrating is a light input storage cathode ray tube such as a return beam vidicon having a target comprised of photosensitive elements responsive to the integral of light intensity and providing long-term electron beam television-type scan readout of said stored attenuation amplitude distribution to said display means.

33. The system of claim 31 wherein:

said display means is a television-type cathode ray tube monitor operating in synchronism with said readout scan and displaying said charge amplitude distribution readout as shades of gray, being said reconstructed x-ray image of said object cross-section.

34. The system of claim 29 wherein:

said laser beam scanner forming said linear projection attenuation signal profiles from said x-ray detector signal sequence at said perpendicular lines includes means for compensating said signal sequence to anticipate and correct for said superfluous spread amplitude distribution of said spatial correlation and storage integration, said compensator being responsive to the level difference of successive said signals, said level differences being integrated in a storage means having an equal charging and discharging rate time constant, said rate being amplitude and polarity sensed and added proportionately to said signal sequence and for a reversed said signal sequence forming compensated signal sequences for 360 degrees said correction of object images, said compensated signal sequence intensity modulating said laser beam scanner forming a compensating said linear projection attenuation profile, said x-ray opaque cylindrical object volume generating a rectangular shaped said linear project attenuation intensity profile signal sequence being said compensated modulating said laser beam with a compensating signal sequence forming a linear projection intensity profile effectively the sum of said rectangular profile and an inverted gaussian-shaped profile in said temporary storage photo-sensitive planar array, said inverted gaussian-shaped profile component being said spatially correlated and integrated as a like inverted gaussian-amplitude distribution integrating with said superfluous spread amplitude distribution to a constant level distribution having said cylindrical amplitude distribution superposed, said uniform density elemental cylindrical object volume being like corrected, said typical human object cross-section amplitude distributions which could be represented by constituent uniform densities cylindrical objects, being like corrected, the present means said rate time constant and said proportional rate addition being optimally adjustable for said typical human cross-section reconstructed images.

35. The system of claim 34 wherein:
said means for compensating said signal sequence is a compensating circuit composed of: an input amplifier for receiving said signal sequences, followed by a resistive divider having a capacitive shunt from said divided input to said divider point, an adjustable constant voltage bias source, a summing amplifier connected to said divider point and said voltage source, and said summing amplifier output signal transmitted to intensity modulate said laser beam, means for reading out in reverse sequence and with reverse laser beam deflection said momentarily stored x-ray detector signals, positive going level differences of successive signals in said sequence being shunted by said capacitor to said divided point, said capacitor being current charged by said level differences for said charging rate time constant, negative going level differences current discharging said capacitor at same said rate, said charging and discharging current into said divided point adding or subtracting to the proportional divided level of said input signal sequence, for a positive going said rectangular profile signal sequence said capacitor is charged at said rate for the duration of said rectangle, at the cessation of said rectangle the said negative going input level difference is shunted by said capacitor to said divided point followed by said discharge, said bias voltage value summed in said summing amplifier being adjusted for positive said laser beam modulation, said compensated laser beam modulation generating said image line signals said temporarily stored, said reversed x-ray detector signal sequence generating like compensated image line signals in reversed direction being like temporarily stored.

36. The system of claim 34 wherein:
said reversed signal sequences are generated by operation of said x-ray object cross-section system for 360 degrees of said x-ray beam fan pattern rotational angle, the first said 180 degree operation is repeated for an additional 180 degrees whereby said reversed signal sequences are effectively generated for generation of said compensation for said 360 degrees correction of said superfluous image spread.

* * * * *